(12) United States Patent
Torella et al.

(10) Patent No.: US 11,021,530 B2
(45) Date of Patent: Jun. 1, 2021

(54) ANTIBODY PREPARATION

(71) Applicant: Hexal AG, Holzkirchen (DE)

(72) Inventors: Claudia Torella, Oberhaching (DE); Benjamin Hackner, Oberhaching (DE); Carsten Funke, Oberhaching (DE); Michael Otten, Oberhaching (DE); Christina Hildebrandt, Oberhaching (DE); Renate Lafuntal, Oberhaching (DE); Florian Wolschin, Oberhaching (DE)

(73) Assignee: Hexal AG, Holzkirchen (DE)

( * ) Notice: Subject to any disclaimer, the term of this patent is extended or adjusted under 35 U.S.C. 154(b) by 0 days.

(21) Appl. No.: 16/345,783

(22) PCT Filed: Oct. 30, 2017

(86) PCT No.: PCT/EP2017/077774
§ 371 (c)(1),
(2) Date: Apr. 29, 2019

(87) PCT Pub. No.: WO2018/078158
PCT Pub. Date: May 3, 2018

(65) Prior Publication Data
US 2020/0055923 A1 Feb. 20, 2020

(30) Foreign Application Priority Data

Oct. 31, 2016 (EP) .................................... 16196544

(51) Int. Cl.
| C07K 16/22 | (2006.01) |
| C07K 16/06 | (2006.01) |
| C07K 1/18 | (2006.01) |
| C07K 1/22 | (2006.01) |

(52) U.S. Cl.
CPC ............ *C07K 16/065* (2013.01); *C07K 16/22* (2013.01); *C07K 2317/24* (2013.01); *C07K 2317/41* (2013.01); *C07K 2317/55* (2013.01); *C07K 2317/565* (2013.01); *C07K 2317/73* (2013.01); *C07K 2317/732* (2013.01); *C07K 2317/76* (2013.01); *C07K 2317/92* (2013.01)

(58) Field of Classification Search
CPC .. C07K 16/065; C07K 16/22; C07K 2317/24; C07K 2317/41; C07K 2317/55; C07K 2317/565; C07K 2317/73; C07K 2317/732; C07K 2317/76; C07K 2317/92; C07K 2317/14; C07K 2317/70; C07K 1/18; C07K 1/22; C07K 1/26; C07K 1/36; C07K 1/16; C07K 1/165; G01N 30/96; G01N 33/684; G01N 33/6857; G01N 33/58; G01N 33/563; G01D 15/362; B01N 15/34; H01J 49/004

See application file for complete search history.

(56) References Cited

U.S. PATENT DOCUMENTS

| 6,054,297 | A | 4/2000 | Carter et al. | |
| 6,632,926 | B1* | 10/2003 | Chen | A61P 43/00 530/387.3 |
| 2007/0264193 | A1* | 11/2007 | Shojaei | C07K 16/28 424/9.1 |
| 2007/0287160 | A1* | 12/2007 | Chou | G01N 33/5005 435/7.2 |
| 2009/0148435 | A1* | 6/2009 | Lebreton | A61P 19/08 424/130.1 |
| 2011/0294150 | A1* | 12/2011 | Koll | C07K 16/00 435/23 |
| 2012/0100166 | A1* | 4/2012 | Roschke | C07K 14/47 424/185.1 |

FOREIGN PATENT DOCUMENTS

WO 2015184403 A2 12/2015

OTHER PUBLICATIONS

Monnet et al., Frontier in Immunology 6: 1-14 (Year: 2015).*
Arnett, Samantha O., et al., IBC's 21st Annual Antibody Engineering and 8th Annual Antibody Therapeutics International Conferences and 2010 Annual Meeting of The Antibody Society, Meeting Report, 2011.
Higel, Fabian Benjamin, Pharmacokinetic Profiling of Therapeutic Proteins and Variants by Mass Spectrometry, Dissertation, Villingen-Schwenningen,Germany, 2014.
Higel, Fabian, et al., N-glycosylation heterogeneity and the influence on structure, function and pharmacokinetics of monoclonal antibodies and Fc fusion proteins, European Journal of Pharmaceutics and Biopharmaceutics, 2016, pp. 94-100.
International Search Report and Written Opinion for PCT/EP2017/077774, dated Mar. 5, 2018, 13 pages.
Zhao, Yan-Yan, et al., Charge Variants of an Avastin Biosimilar Isolation, Characterization, In Vitro Properties and Pharmacokinetics in Rat, PLoS ONE, vol. 11, No. 3, Mar. 17, 2016, 13 pages.

* cited by examiner

*Primary Examiner* — Phuong Huynh
(74) *Attorney, Agent, or Firm* — Luedeka Neely Group, P.C.

(57) ABSTRACT

The present invention relates to the field of biotechnology, and in particular to the field of antibodies. Provided herein are novel methods for removing glycosylated antibody variants from an antibody preparation, an antibody preparation obtained by said method, and a pharmaceutical composition comprising the same.

Figure 1:
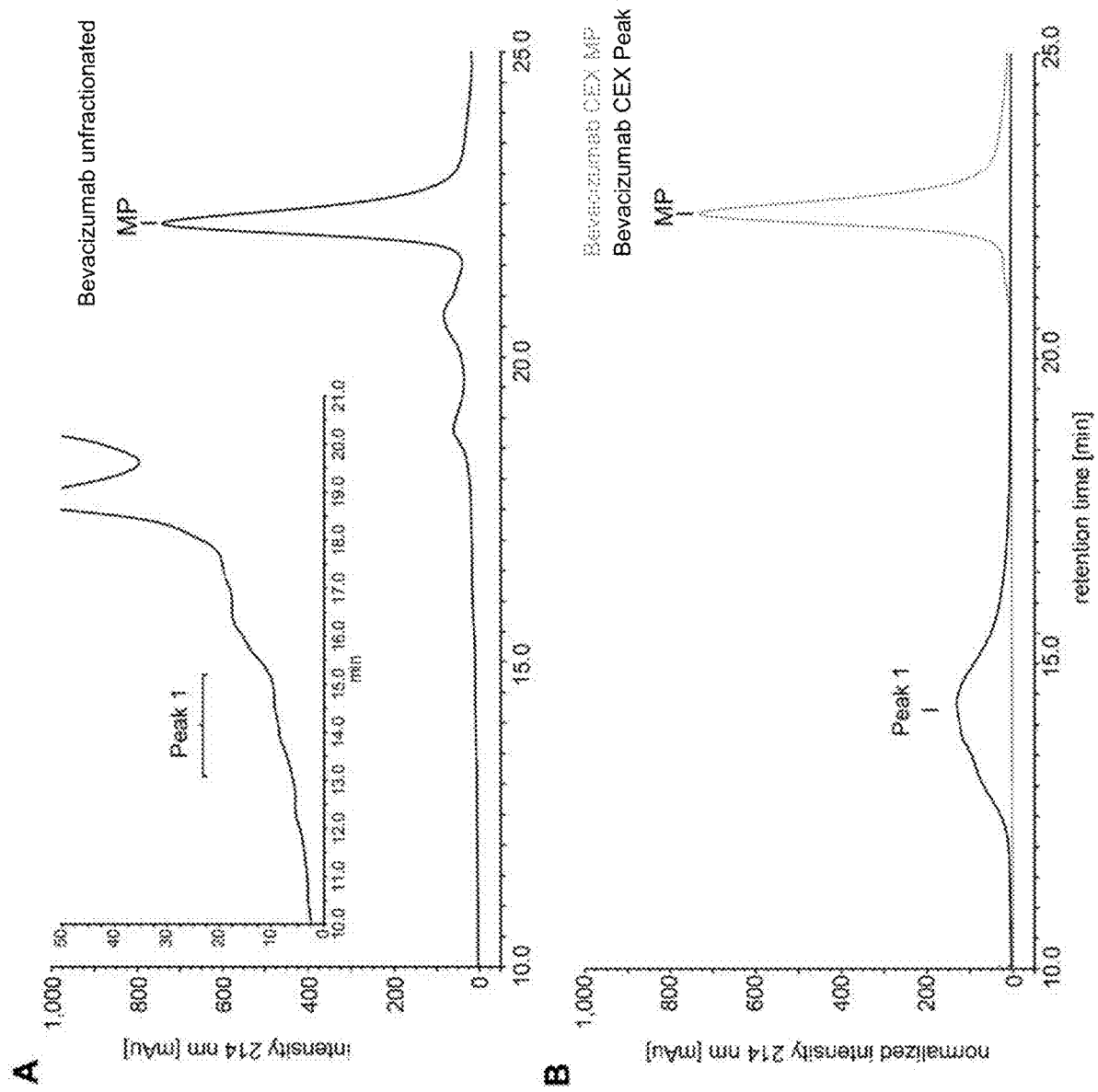

8 Claims, 11 Drawing Sheets
Specification includes a Sequence Listing.

Figure 9

| | |
|---|---|
| N-glycosylation consensus motif: | N*XS/T (X ≠ P) |
| Example (canonic IgG1 glycosylation site): | EQFN*STF |
| | |
| N-glycosylated sites not adhering to the consensus motif according to literature[1]: | VSWN*SGA |
| | MTKN*QVS |
| | SSSN*ENF |
| | QSGN*SQE |
| | |
| N-glycosylated site not adhering to the consensus motif found in bevacizumab: | TFTN*YGM |

[1] Valliere-Douglass et al (2010) J.Biol.Chem. 285, 16012-16022.

SEQUENCE LISTING

```
<160> NUMBER OF SEQ ID NOS: 8

<210> SEQ ID NO 1
<211> LENGTH: 11
<212> TYPE: PRT
<213> ORGANISM: artificial
<220> FEATURE:
<223> OTHER INFORMATION: CDR-H1

<400> SEQUENCE: 1

Ser Gly Tyr Thr Phe Thr Asn Tyr Gly Met Asn
1               5                   10

<210> SEQ ID NO 2
<211> LENGTH: 17
<212> TYPE: PRT
<213> ORGANISM: artificial
<220> FEATURE:
<223> OTHER INFORMATION: CDR-H2

<400> SEQUENCE: 2

Trp Ile Asn Thr Tyr Thr Gly Glu Pro Thr Tyr Ala Ala Asp Phe Lys
1               5                   10                  15

Arg

<210> SEQ ID NO 3
<211> LENGTH: 13
<212> TYPE: PRT
```

```
<213> ORGANISM: artificial
<220> FEATURE:
<223> OTHER INFORMATION: CDR-H3

<400> SEQUENCE: 3

Tyr Pro His Tyr Tyr Gly Ser Ser His Trp Tyr Phe Asp
1               5                   10

<210> SEQ ID NO 4
<211> LENGTH: 11
<212> TYPE: PRT
<213> ORGANISM: artificial
<220> FEATURE:
<223> OTHER INFORMATION: CDR-L1

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: artificial
<220> FEATURE:
<223> OTHER INFORMATION: CDR-L2

<400> SEQUENCE: 5

Phe Thr Ser Ser Leu His Ser
1               5

<210> SEQ ID NO 6
<211> LENGTH: 9
<212> TYPE: PRT
<213> ORGANISM: artificial
<220> FEATURE:
<223> OTHER INFORMATION: CDR-L3

<400> SEQUENCE: 6

Gln Gln Tyr Ser Thr Val Pro Trp Thr
1               5

<210> SEQ ID NO 7
<211> LENGTH: 453
<212> TYPE: PRT
<213> ORGANISM: artificial
<220> FEATURE:
<223> OTHER INFORMATION: VH region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110
```

```
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 8
<211> LENGTH: 214
<212> TYPE: PRT
<213> ORGANISM: artificial
<220> FEATURE:
<223> OTHER INFORMATION: VL region

<400> SEQUENCE: 8

Asp Ile Gln Met Thr Gln Ser Pro Ser Ser Leu Ser Ala Ser Val Gly
1               5                   10                  15
```

-continued

```
Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTIBODY PREPARATION

This application is a Section 371 national phase entry of PCT application PCT/EP2017/077774, filed Oct. 30, 2017. This application also claims the benefit of the earlier filing date of European patent application 16196544.7, filed Oct. 31, 2016.

This application contains a Sequence Listing which has been submitted electronically in ASCII format and is herein incorporated by reference. The ASCII file, created on Apr. 3, 2019, is named 74417us-topto-20190429-SequenceListing.TXT, and is 7172 bytes in size.

Immunoglobulins (IgGs) undergo a large number of modifications, arguably the most important and complex one being nitrogen-linked glycosylation (N-glycosylation). N-glycosylation can occur at several sites within a biotherapeutic and may significantly influence physicochemical and biological properties such as efficacy and safety.

N-glycosylation is carried out mainly on Asn (asparagine) residues in a co-translational/trans-locational manner by the oligosaccharyl transferase (OST) complex. With high specificity the enzyme complex catalyzes the transfer of an oligosaccharyl moiety ($Glc_3Man_9GlcNAc_2$) from the dolichol-linked pyrophosphate donor to the side chain's functional group of Asn, within a consensus sequence of Asn-X-Thr/Ser, where X can be any amino acid except for proline. However, non-canonical N-glycosylation sequence motifs have been described (Valliere-Douglass, et al. 2009, J. Biol. Chem. 284, 47: 32493-32506, Valliere-Douglass, et al. 2010, J. Biol. Chem. 285, 21: 16012-16022, Anal. Chem. 82,24: 10095-10101, Zhang et al. 2010, J. Proteome Res. 14: 2633-2641, Asperger et al. 2015).

Sometimes, glycosylated variants of a protein such as an antibody may not necessarily be desirable. Although such variants may not necessarily be troublesome, it could nevertheless be desirable to remove or avoid them, if they are present in a large amount.

The technical problem underlying the present application may therefore be seen in the provision of means and methods for reducing, if necessary, potentially undesired glycosylated variants of an antibody. The solution is reflected in the claims explained herein and illustrated in the Examples and Figures.

The present invention concerns a novel N-glycosylation site in the complementarity determining region 1 (CDR-H1) of the humanized IgG1 heavy chain of bevacizumab. The respective glycopeptide was identified by reversed phase liquid chromatography mass spectrometry (RP-LC-MS) following enrichment via cation exchange chromatography (CEX), lectin-affinity purification (LAP), or size exclusion chromatography (SEC) and the glycosylation site was pinpointed using MS/MS. The identified N-glycosylation site is not associated with any known consensus rules. It was shown that this glycosylation consists of mostly the complex-, core-fucosylated-, bi-, tri- and tetra-antennary- and sialylated-type. Binding studies based on surface plasmon resonance (SPR) and in vitro potency assays revealed an altered target binding and activity profile of fractions highly enriched in the novel variant compared to the main peak fraction.

SUMMARY

The present invention provides a method for reducing the amount of a CDR-H1 glycosylated antibody variant that competes for binding to human VEGF-A with the antibody bevacizumab in a preparation comprising said antibody variant, comprising (i) subjecting said preparation to cation exchange chromatography (CEX), size exclusion chromatography (SEC) or lectin affinity purification (LAP), (ii) analyzing fractions obtained in step (i) for the presence of said CDR-H1 glycosylated antibody variant by HPLC-MS (/MS); and (iii) removing fractions comprising said CDR-H1 glycosylated antibody variant.

The method may further comprise adjusting the purification process for bevacizumab, preferably based on the analysis of fractions obtained in step (i), for example, adjustment of splitting criteria for the CEX-step and/or introducing a SEC purification step can facilitate the removal of this variant during manufacturing.

Competition for binding to human VEGF-A can be measured by ELISA, flow cytometry or surface plasmon resonance (SPR) assay.

The glycosylated antibody variant is envisaged to comprise a CDR-H1 having the amino acid sequence shown in SEQ ID NO:1 (SGYTFTNYGMN), wherein the N is glycosylated; said N-glycosylation can in particular be a complex type glycosylation that for instance includes core-fucosylated, bi-antennary, tri-antennary, tetra-antennary and/or sialylated glycans.

The CDR-H1 glycosylated antibody variant may be characterized in that it (i) has a reduced binding affinity to VEGF in comparison to a non-CDR-H1 glycosylated variant and/or (ii) shows a reduced inhibition on the VEGF-dependent proliferation of HUVEC cells in comparison to a non-CDR-H1 glycosylated variant.

Said antibody may comprise a CDR-H1 shown in SEQ ID NO: 1, CDR-H2 shown in SEQ ID NO: 2, CDR-H3 shown in SEQ ID NO: 3, CDR-L1 shown in SEQ ID NO: 4, CDR-L2 shown in SEQ ID NO: 5 and CDR-L3 shown in SEQ ID NO: 6. It may comprise a VH region having the amino acid sequence shown in SEQ ID NO: 7 and a VL region having the amino acid sequence shown in SEQ ID NO: 8.

Said antibody may be humanized, and may in particular be bevacizumab. The antibody may be an antibody fragment, such as Fab, Fab', $F(ab')_2$, scFV, di-scFv, VHH or VH. It may have an IgG isotype, such as IgG1 or IgG2.

The antibody may include one or more mutations in the Fc region that increase ADCC activity and/or include one or more mutations in the Fc region that either increase binding to FcγR or that increase binding to FcRn. It may include one or more mutations in the Fc region that decrease ADCC activity.

The invention further provides an antibody preparation obtainable by the method described herein. Also provided herein is an antibody-drug conjugate comprising said antibody. Said antibody or antibody-drug conjugate may in particular be used for treating neo-vascularization or pathological angiogenesis.

The invention further relates to a pharmaceutical composition comprising the antibody or the antibody-drug conjugate, and a pharmaceutically acceptable carrier.

FIGURES

FIG. 1: CEX analysis of bevacizumab (chromatogram at 214 nm). Panel A) Unfractionated sample. The indicated peaks were fractionated: MP=main peak and peak 1 (zoomed chromatogram in inset). Panel B) Re-chromatography of the fractionated peak 1 (black) and MP (gray).

Figure 2:
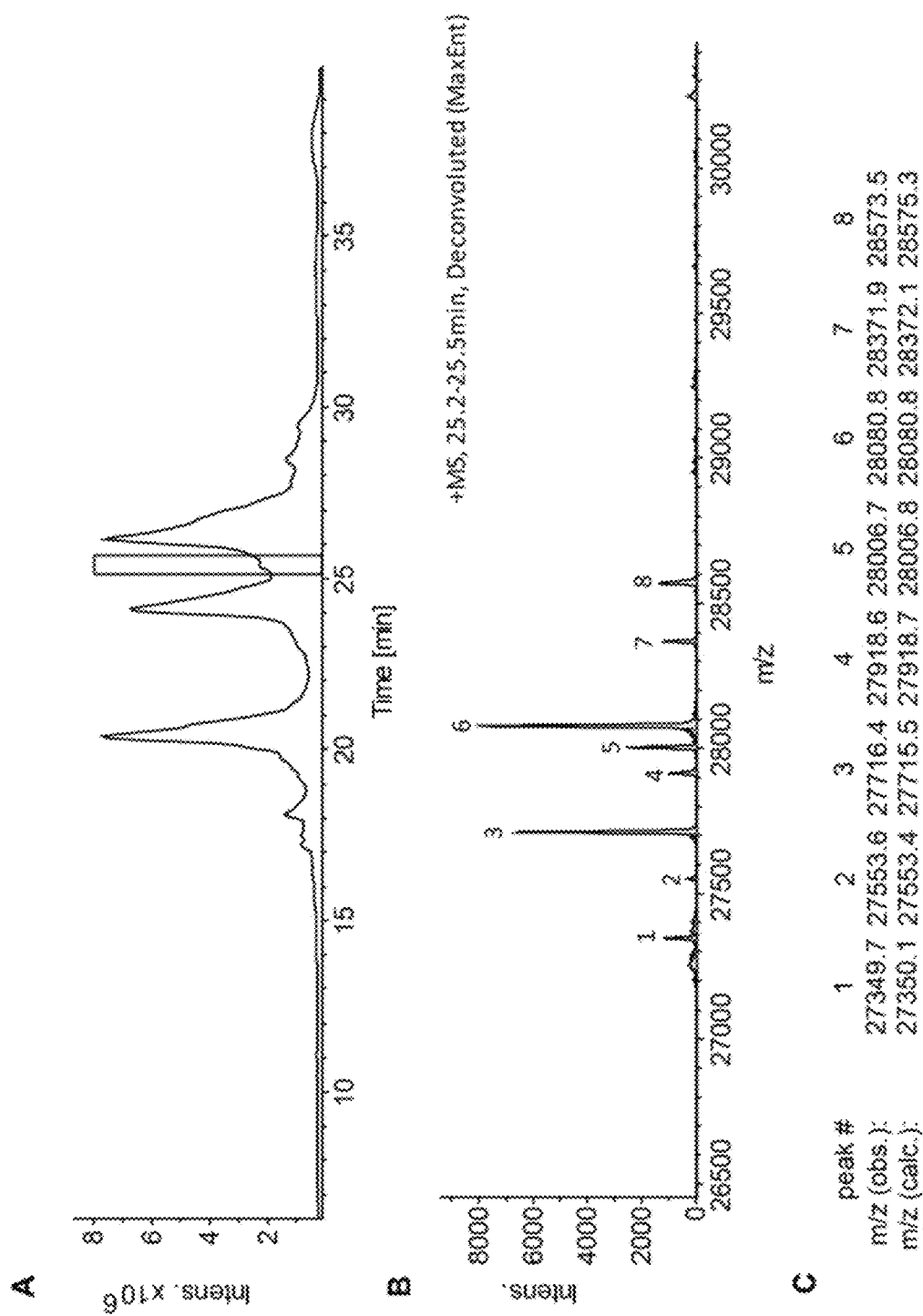

FIG. 2: RP-LC-MS analysis of the CEX-isolated peak 1 (see FIG. 1) digested with Immunoglobulin G-degrading enzyme of Streptococcus pyogenes (IdeS) and reduced.

Panel A) Total ion chromatogram (TIC) of the RP-LC-MS analysis. The rectangle highlights the fragment identified as glycosylated heavy chain fragment [1-242] of bevacizumab. Panel B) Deconvoluted mass spectrum corresponding to the highlighted chromatographic peak; the masses of the numbered peaks are shown in panel C. Panel C) Observed masses with assignment to calculated masses for different glycoforms of heavy chain fragment [1-242] of bevacizumab (glycoform assignment in Table 1).

Figure 3:
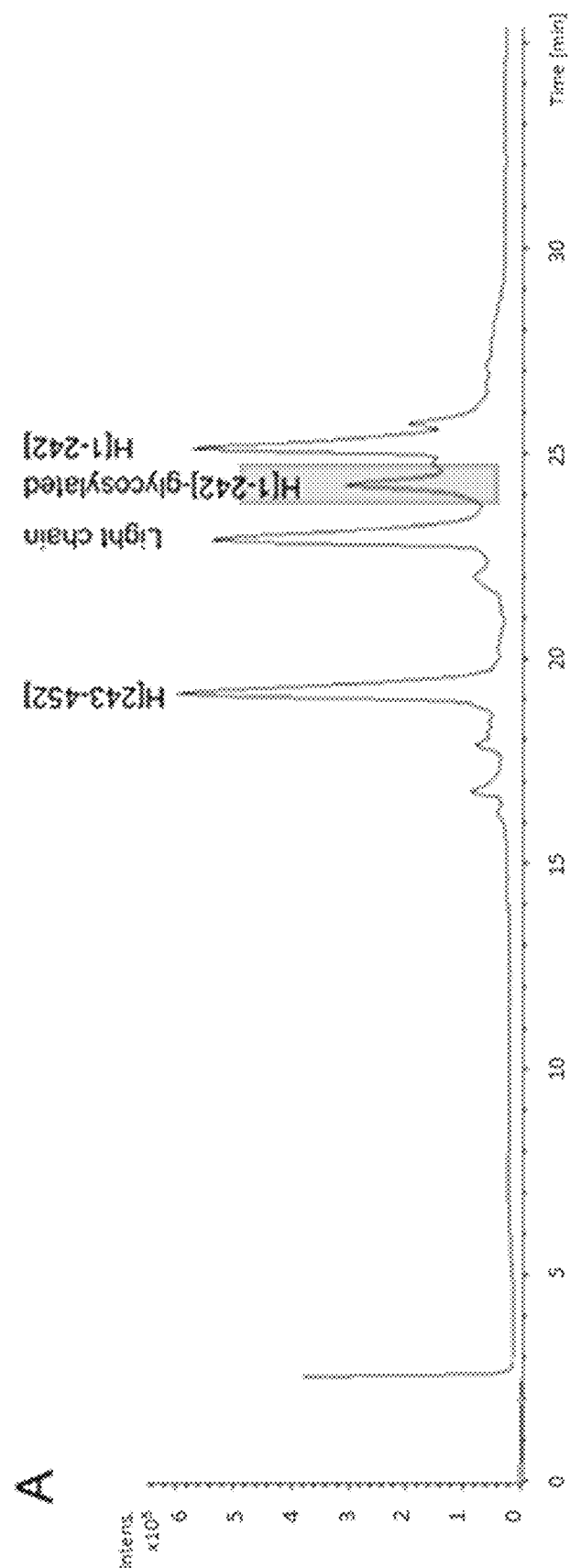
Figure 3:
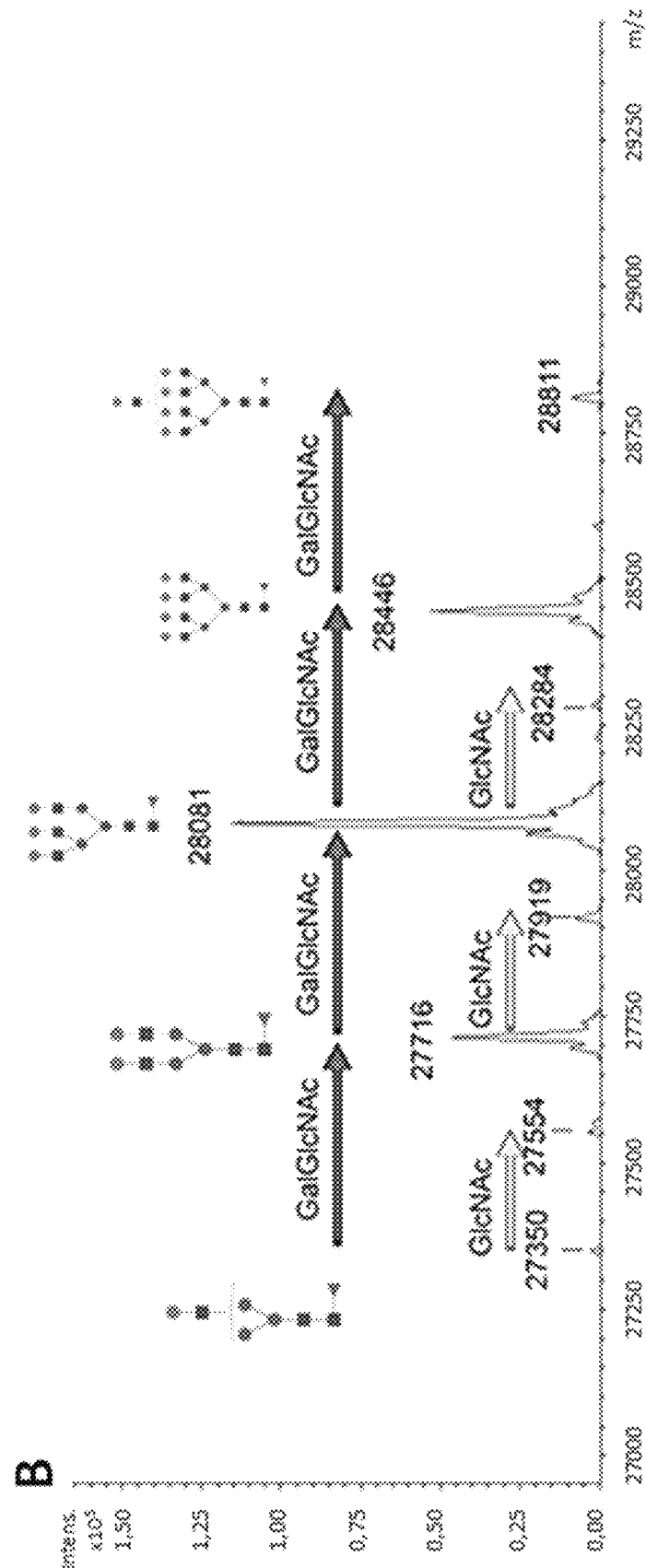

FIG. 3: RP-LC-MS analysis of a Fab-glycosylated bevacizumab enriched by LAP, digested with Immunoglobulin G-degrading enzyme of *Streptococcus pyogenes* (IdeS) and reduced. Panel A) Total ion chromatogram (TIC) of the RP-LC-MS analysis. The rectangle highlights the fragment identified as glycosylated heavy chain [1-242] of bevacizumab. Panel B) Deconvoluted mass spectrum corresponding to the highlighted chromatographic peak with indication of the observed masses. The respective glycosylation pattern of fragment [1-242] is annotated and the increase of building blocks indicated with arrows. Refer to Table 1 for assignment of glycan structures (asialo structures). GlcNAc=HexNAc; Gal=antennary Hex; NeuNAc=sialic acid.

Figure 4:
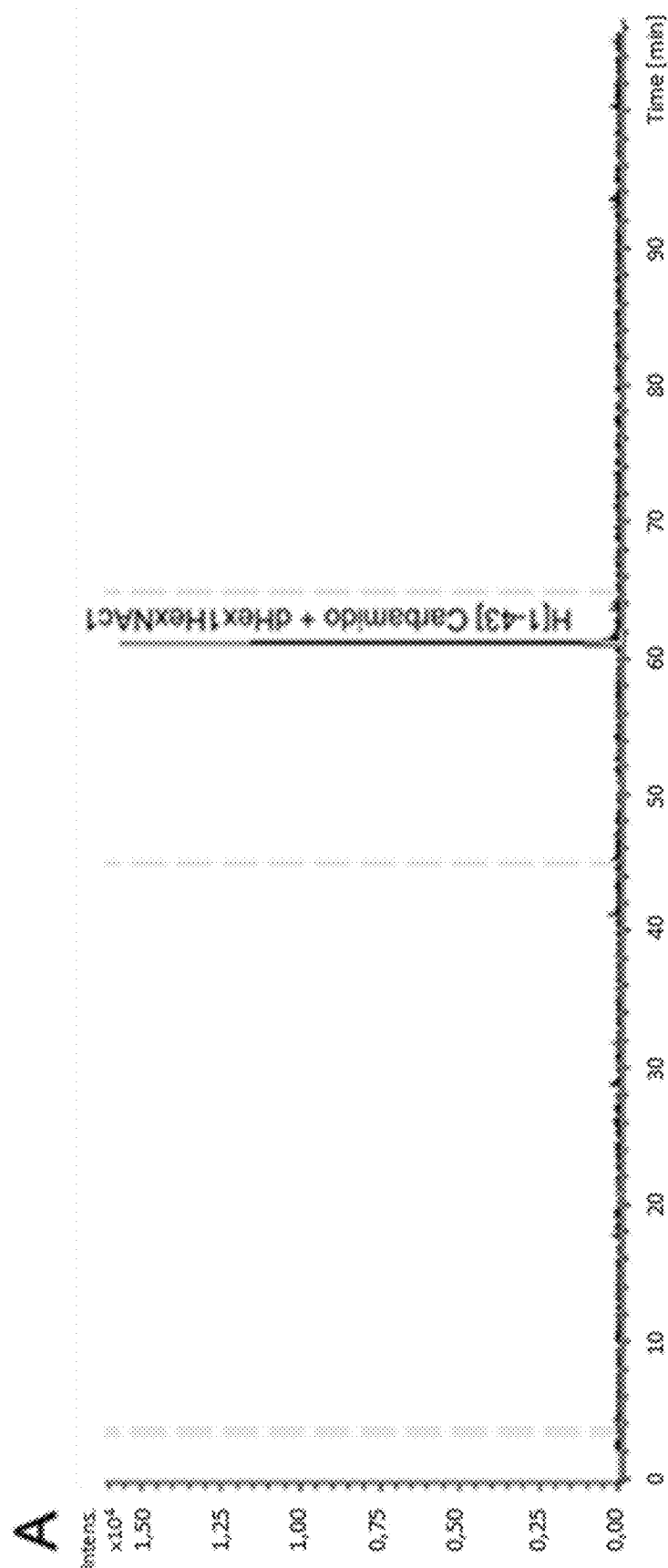
Figure 4:
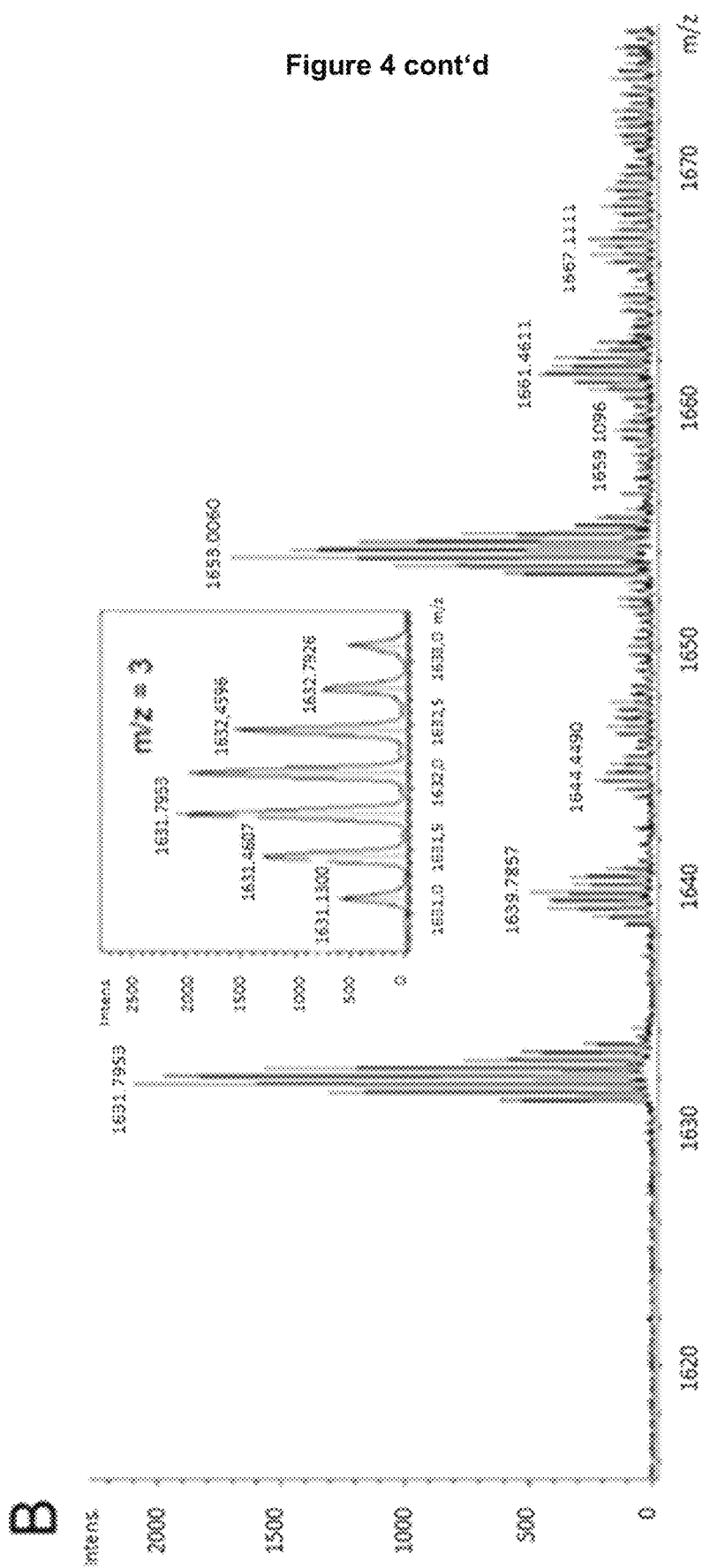

FIG. 4: RP-LC-MS analysis of the endoprotease LysC digest of LAP-enriched bevacizumab, which was also digested with endoglycosidase Endo-F2 to reduce glycosylation complexity. Panel A) Extracted ion chromatogram (EIC) for the alkylated (carbamidomethylated), dHex1HexNAc1 modified heavy chain peptide [1-43]. Panel B) Averaged mass spectrum for RT 61.2-61.4 min, zoomed to m/z 1615-1675. The peak pattern for the MH[+3] ion at m/z 1621.130 and isotopologues is depicted in the inset.

Figure 5:
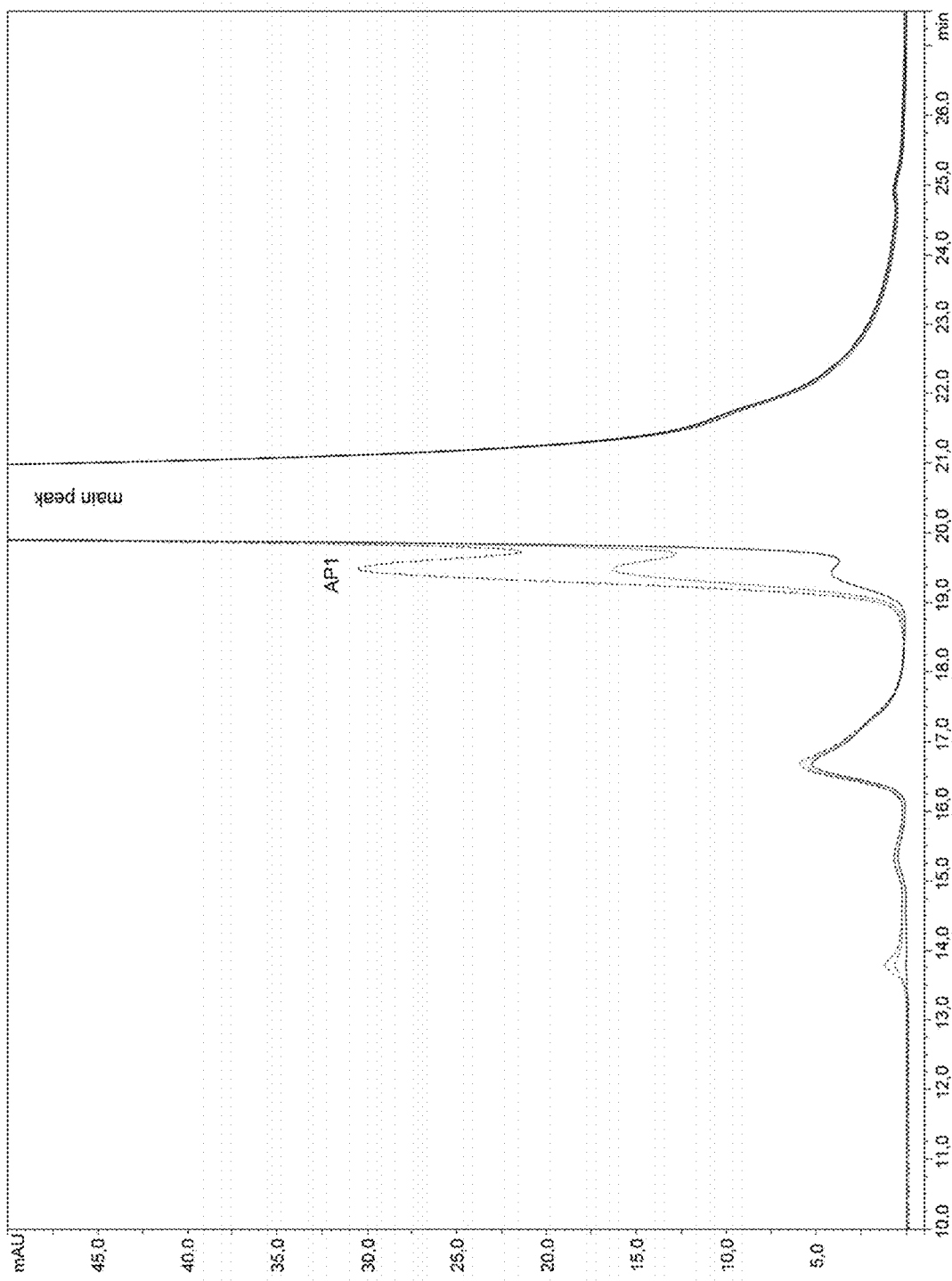

FIG. 5: SEC analysis of a bevacizumab sample spiked with LAP-enriched material at different concentrations. An increased spiked amount of LAP-enriched material (dotted lines) is accompanied by an increase of the peak AP1 left of the main SEC peak (main antibody form) compared to the non-spiked bevacizumab sample (solid line).

Figure 6:
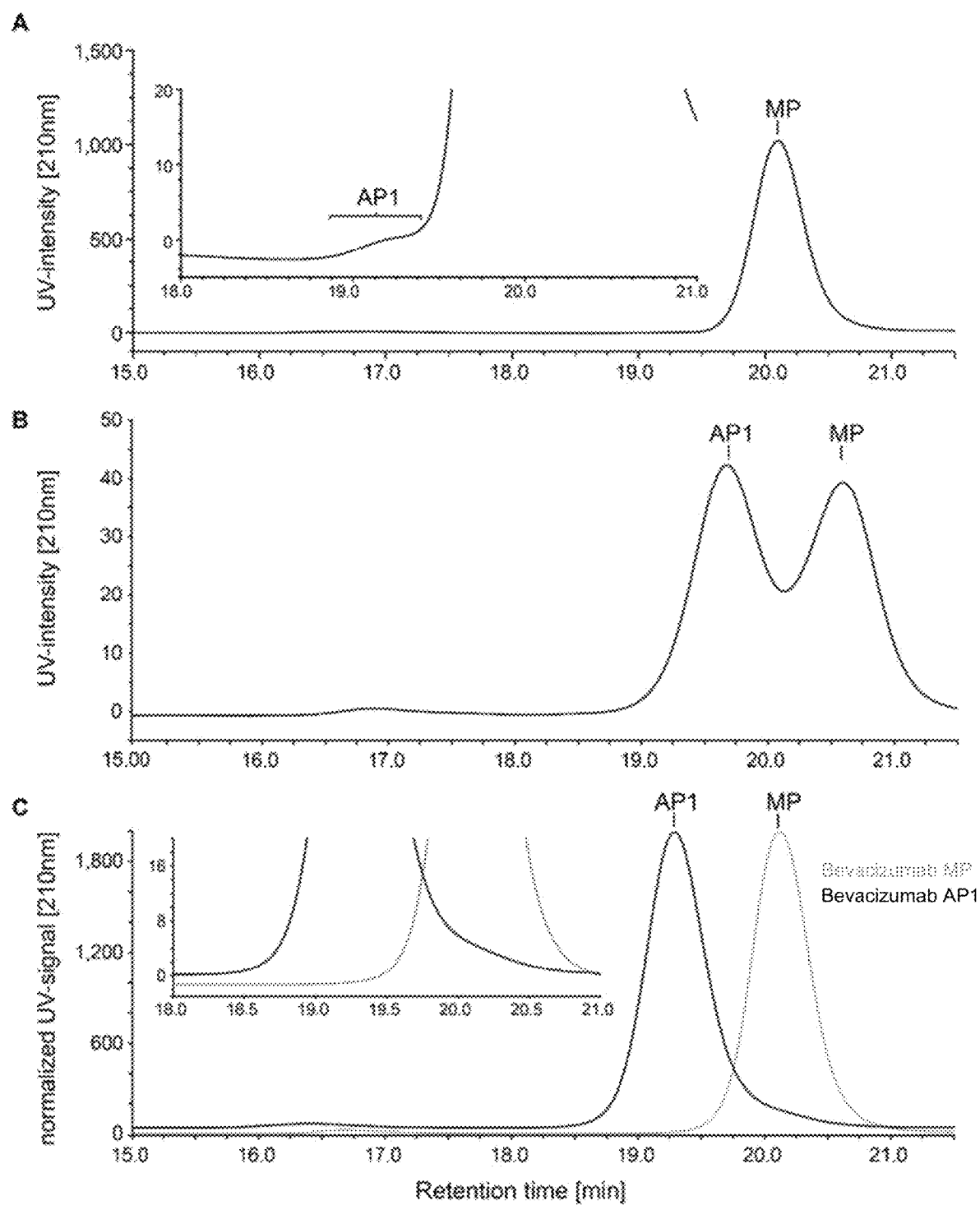

FIG. 6: SEC fractionation of AP1 and main peak (MP) from a bevacizumab sample. Panel A) Unfractionated sample. Inset: zoom into the left shoulder of the main peak, where the shoulder AP-1 is clearly visible. Panel B) SEC re-chromatography of a partially purified SEC AP1 peak. AP1 is strongly enriched but the main peak is still present. Panel C) SEC re-chromatography (overlay) of purified MP (gray) and highly enriched bevacizumab SEC AP1 peak (black). Inset: zoom showing that the purified MP does not contain the shoulder AP1 anymore. The highly purified AP1 fraction was analyzed in the anti-proliferation assay (Table 7).

Figure 7:
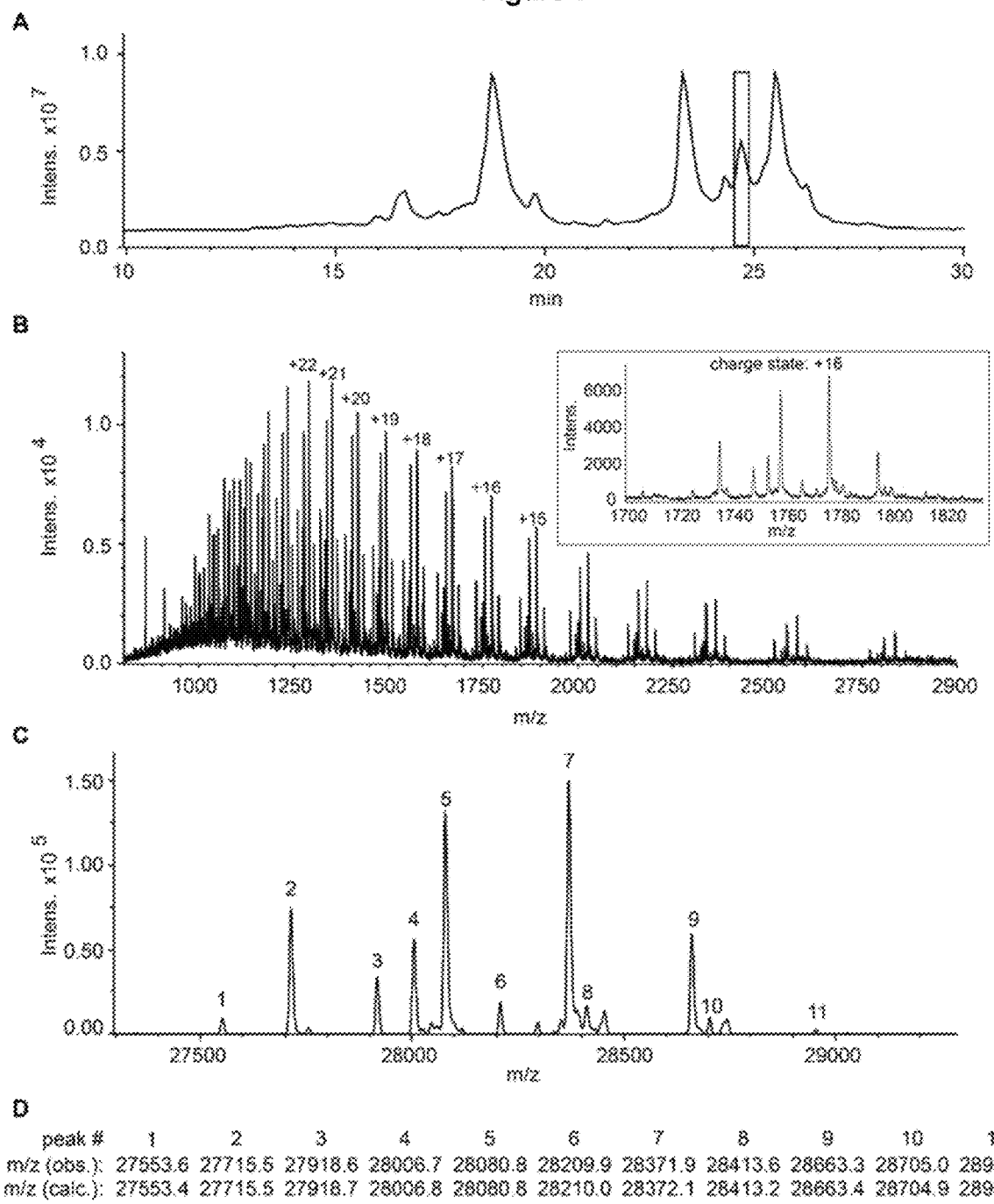

FIG. 7: RP-LC-MS analysis of the enriched bevacizumab SEC AP1 fraction, digested with IdeS and reduced. Panel A) Total ion chromatogram; the highlighted peak corresponds to the fragment identified as glycosylated heavy chain [1-242] of bevacizumab (mass spectrum in panel B). Panel B) Averaged spectrum corresponding to the highlighted chromatographic peak. Inset: zoom of the spectrum for the charge state+16. Panel C) Deconvoluted mass spectrum; the masses of the numbered peaks are shown in panel D. Panel D) Observed masses with assignment to calculated masses for different glycoforms of heavy chain fragment [1-242] of bevacizumab (glycoform assignment in Table 4).

Figure 8:
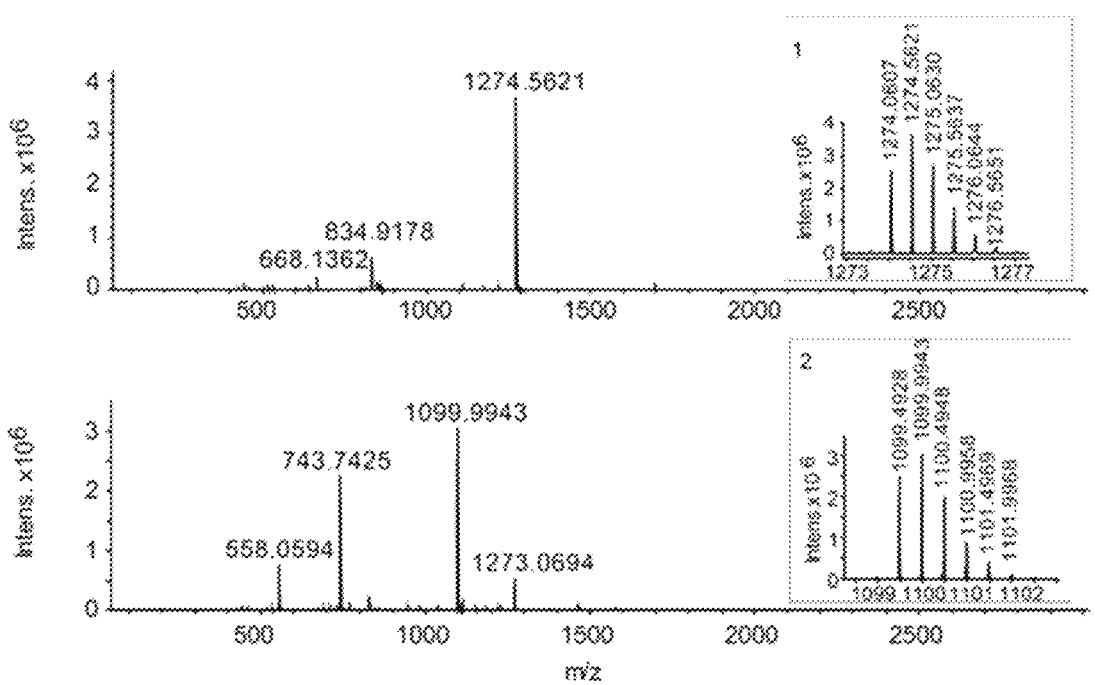

FIG. 8: RP-LC-MS/MS analysis of the tryptic digests of the enriched SEC AP1 fraction of bevacizumab, also digested with endoglycosidase EndoF to reduce glycosylation complexity. Panel A) extracted ion chromatograms of the peptides in the table inset (1=glycosylated, 2=unmodified), including the retention time and calculated/observed masses. Unmodified peptide in gray, modified peptide in black (modified amino acid indicated with *. For identification of peptides and non-consensus glycosylation site (NCGs) see panel B-D) in black. Panel B) Summed MS spectra corresponding to peak 1 (glycosylated peptide); inset: zoom of the spectrum for the charge state+2 with isotopic distribution. Panel C) summed MS spectra corresponding to peak 2 (unmodified peptide); inset: zoom of the spectrum for the charge state+2 with isotopic distribution. Panel D) CID MS/MS spectra of the glycosylated peptide (panel B) with annotation of b-ion series (in gray) and y-ion series (in black) and identification of the peptide and the glycosylation site (N*).

FIG. 9: Comparison of known glycosylation variants with the new N-glycosylation site found in bevacizumab.

DETAILED DESCRIPTION

The present inventors identified a novel N-glycosylation site in the complementarity determining region 1 (CDR-H1) of the humanized IgG1 heavy chain of bevacizumab. A method for reducing the amount of antibodies carrying the novel N-glycosylation ("glycosylated antibody variants") is provided herein that is envisaged to yield a preparation of antibodies that are free or substantially free of said N-glycosylation.

Therefore, a method for reducing the amount of a CDR-H1 glycosylated antibody variant that competes for binding to human VEGF-A with the antibody bevacizumab in a preparation comprising said antibody variant is provided herein. Said method comprises the steps of (i) subjecting said preparation to cation exchange chromatography (CEX), size exclusion chromatography (SEC) or lectin affinity purification (LAP), (ii) analyzing fractions obtained in step (i) for the presence of said CDR-H1 glycosylated antibody variant by HPLC-MS; and (iii) removing fractions comprising said CDR-H1 glycosylated antibody variant. The CDR-H1 glycosylated antibody variant is envisaged to comprise a CDR-H1 having the amino acid SEQ ID NO: 1 (SGYTFTNYGMN) wherein the first asparagine (N) is glycosylated.

Specifically, the inventors found that the N-glycosylation site of SEQ ID NO:1 does not adhere to a known consensus motif, as can be seen from Table 1 below and FIG. 9.

TABLE 1

Consensus and non-consensus N-glycosylation sites

| N-glycosylation consensus motif | N-glycosylation sites not adhering to the consensus motif from literature[1] | N-glycosylation site not adhering to the consensus motif found by the inventors in bevacizumab |
|---|---|---|
| NXS/T (X ≠ P) Example: EQFN*STF | VSWN*SGA MTKN*QVS SSSN*ENF QSGN*SQE | TFTN*YGM |

[1]Valliere-Douglass et al (2010) J.Biol.Chem. 285, 16012-16022.

The glycosylated N is marked as N* in the table above. In detail, the known N-glycosylation motifs generally adhere to the consensus motif NXS/T(X≠P). As cited above, four N-glycosylation sites are known from other antibodies that do not adhere to this consensus motif, however there is no similarity to the new N-glycosylation site found in bevacizumab. Such non-canonical glycosylation sites are the exception, rather than the rule. The N-glycosylation site from bevacizumab is TFTN*YGM, which is distinct both from the known consensus sequence and from the known other divergent N-glycosylation sites from other antibodies. While it is generally accepted that many antibodies have N-glycosylation sites, such glycosylation variants generally fall under the known consensus motif and are therefore easy to identify. For bevacizumab, the glycosylation motif is unexpected as is its position within the antibody. While glycosylation variants are generally undesirable, the skilled person would not have assumed a glycosylation variant such as that identified in bevacizumab simply by looking at the antibody sequence. It was only the experiments performed by the inventors that allowed for the identification of the glycosylation variant, which in turn led to the claimed methods for removing such CDR-H1 glycosylated antibody variants to improve the bevacizumab compositions.

Method Steps

The inventive method comprises several steps for reducing the amount of CDR-H1 glycosylated antibodies in an antibody preparation. First, the antibody preparation comprising said glycosylated variant is subjected to either cation exchange chromatography (CEX), size exclusion chromatography (SEC) or lectin affinity purification (LAP), as described in the appended Examples. Briefly, cation exchange chromatography (CEX) is a form of ion exchange chromatography (IEX) which is used to separate molecules based on their net surface charge. Size Exclusion Chromatography (SEC) achieves separation of molecules based on their molecular size. Lectin affinity purification (LAP) exploits the different affinities of glycan structures on proteins to interact with immobilized lectins. Different antibody variants (i.e., CDR-H1 glycosylated versus non-glycosylated) are envisaged to elute as distinct fractions that are subsequently subjected to HPLC-MS in order to identify CDR-H1 glycosylated antibody variants as described in the appended Examples. A further step of purifying and/or enriching the obtained fraction can precede the HPLC-MS analysis. Subsequently, fractions comprising CDR-H1 glycosylated antibody can be removed by e.g. ion exchange chromatography.

The present invention is thus useful for screening out antibody variants carrying a CDR-H1 glycosylation as described herein. The term "variant" as used herein refers to a fraction of CDR-H1 glycosylated antibodies present in a preparation of antibodies that are identical except for the CDR-H1 glycosylation. That is, apart from the CDR-H1 glycosylation, all antibodies in the preparation to be subjected to the method of the present invention are envisaged to be identical, i.e. share a common amino acid sequence and post-translational modification (including Fc-glycosylation) pattern. For instance, the antibody preparation to be subjected to the method of the invention may comprise bevacizumab, in particular bevacizumab antibodies comprising the CDR-H1 glycosylation described herein ("glycosylated bevacizumab variants"), and a bevacizumab fraction not comprising said CDR-H1 glycosylation ("non-glycosylated bevacizumab variants"). The inventive method serves to remove glycosylated bevacizumab variants from the overall preparation, thereby reducing their amount. However, it will readily be understood that the method can be used for reducing the amount of any glycosylated antibody variant competing for binding to human VEGF-A with the antibody bevacizumab from a preparation of CDR-H1 glycosylated and non-CDR-H1 glycosylated antibodies otherwise sharing a common amino acid sequence and post-translational modification pattern.

Antibody

As is well known in the art, an antibody is an immunoglobulin molecule capable of specific binding to a target antigen through at least one antigen recognition site, located in the variable region of the immunoglobulin molecule. A "native antibody" is a tetrameric glycoprotein. In a naturally-occurring native antibody, each tetramer is composed of two identical pairs of polypeptide chains, each pair having one "light" chain (about 25 kDa) and one "heavy" chain (about 50-70 kDa). The amino-terminal portion of each chain includes a "(hyper)variable" region of about 100 to 110 or more amino acids primarily responsible for antigen recognition. The variable region comprises amino acid residues from a "complementarity determining region" or CDRs or "CDR regions". "Framework" or FR residues are those variable domain residues other than the hypervariable region residues.

Variable Regions

Both the antibody light and heavy chains are divided into regions of structural and functional homology referred to as the "constant region" and the "variable region". The terms "constant" and "variable" are used functionally. In this regard, it will be appreciated that the variable regions of both the light (VL) and heavy (VH) chains determine antigen recognition and specificity. The terms "VL", "VL region", and "VL domain" are used interchangeably throughout the specification to refer to the variable region of the light chain. Similarly, the terms "VH", "VH region" and "VH domain" are used interchangeably herein to refer to the variable region of the heavy chain.

The VL and VH region, and specifically the subset of the complementarity determining regions (CDRs) within these variable regions of an antibody combine to form a three dimensional antigen binding site. This quaternary antibody structure forms the antigen binding site. More specifically, the antigen binding site is defined by three CDRs (CDR1, CDR2, CDR3, determined following Kabat numbering system) on each of the VH and VL regions. The three CDRs of the light chain are also designated CDR-L1, CDR-L2 and CDR-L3 herein. The three CDRs of the heavy chain are also termed CDR-H1, CDR-H2 and CDR-H3.

The CDR-H1 glycosylated antibody variant to be separated out according to the method of the invention is particularly envisaged to comprise a CDR-H1 having the amino acid sequence shown in SEQ ID NO: 1 (SGYTFTNYGMN), wherein the first asparagine (N) is glycosylated, in particular as described below.

Specifically, it is envisioned that said glycosylated antibody variant preferably comprises a CDR-H1 shown in SEQ ID NO: 1 (SGYTFTNYGMN), a CDR-H2 shown in SEQ ID NO: 2 (WINTYTGEPTYAADFKR), a CDR-H3 shown in SEQ ID NO: 3 (YPHYYGSSHWYFD), a CDR-L1 shown in SEQ ID NO: 4 (SASQDISNYLN), a CDR-L2 shown in SEQ ID NO: 5 (FTSSLHS) and a CDR-L3 shown in SEQ ID NO: 6 (QQYSTVPWT).

The CDR-H1 glycosylated antibody variants may comprise a VH region having the amino acid sequence shown in SEQ ID NO: 7 and a VL region having the amino acid sequence shown in SEQ ID NO: 8.

CDR-H1 Glycosylation

Like most extracellular glycoproteins, therapeutic proteins and specifically antibodies typically undergo glycosylation in the endoplasmatic reticulum (ER) and Golgi apparatus of antibody expressing mammalian host cells. The term "glycosylation" as used herein refers to the addition (and optionally processing) of oligosaccharide (glycan) structures to the reactive group of another molecule, such as an amino acid side chain in an antibody variable or constant region. The sugar monomers are linked to one another in the glycan chain via glycosidic bonds. Attachment of the glycan structure to an antibody typically requires the recognition of a consensus sequence. N-linked glycans are attached to the amide nitrogen in asparagine or arginine side-chains ("N-linked glycosylation" or "N-glycosylation") that is typically present as a part of Asn-X-Ser or Asn-X-Thr consensus sequence, where X is any amino acid except proline (Pro).

The biosynthesis of N-linked glycans occurs via 3 major steps: (1) synthesis of the precursor oligosaccharide, (2) en bloc transfer of precursor oligosaccharide to the protein and (3) processing of the oligosaccharide. The structure of said oligosaccharide precursor is the same in plants, animals, and single-celled eukaryotes—a branched oligosaccharide, containing three glucose (Glc), nine mannose (Man), and two N-acetylglucosamine (GlcNAc) molecules ($Glc_3Man_9(GlcNAc)_2$). Variations in the structures of N-linked oligosaccharides occur as a result of differences in subsequent oligosaccharide processing within the ER and Golgi.

The glycan structures of antibodies can affect their stability and binding behavior and are therefore thought to be of importance for therapeutic efficacy and safety. Whereas N-linked glycosylation in the variable region has been described for some antibodies, research has primarily focused on the one conserved N-linked glycosylation site in the Fc region at position N297 and its effects on modulating antibody effector functions and pharmacokinetics as described elsewhere herein.

The present inventors have, however, identified novel bevacizumab variants bearing a previously unknown glycosylation in the CDR-H1 of the antibody variable region that did not correlate with any known consensus rules, and was shown to affect antigen binding and activity. Said glycosylation is particularly thought to be attached to the first asparagine (N) in the CDR-H1 region of the sequence SGYTFTNYGMN (SEQ ID NO: 1), i.e. to be an N-linked glycosylation, which is further envisioned to be a complex-type glycosylation. The CDR-H1 glycosylation variants present in the bevacizumab described herein are also referred to as "Fd-glycosylated" or "Fab-glycosylated" variants, as the novel glycosylation pattern in the CDR-H1 region is present in the Fab fragment (i.e., the antigen-binding region of an antibody composed of one constant and one variable domain of each of the heavy and the light chain) and the Fd region (i.e., the heavy chain portion of the Fab fragment).

"Complex-type" glycans are so named because they can contain almost any number or combination of saccharide monomers, particularly those selected from sialic acid (N-acetylneuraminic acid, NANA), N-acetylgalactosamine (GalNAc), N-acetylglucosamine (GlcNac), galactose, glucose, mannose and fucose. The complex-type glycosylation of the antibody variant is envisioned to include core-fucosylated, bi-antennary, tri-antennary, tetra-antennary and/or sialylated-type glycosylation. The term "core-fucosylation" refers to addition of a fucose residue to the innermost N-acetylglucosamine monomer. "Bi-, tri- and tetra-antennary" glycans comprise two, three or four oligosaccharide branches linked to the glycan core. "Sialylated" glycans comprise variable amounts of sialic acid.

As set out previously, the CDR-H1 glycosylated antibody variants exhibited an altered binding and activity profile as compared to non-CDR-H1 glycosylated variants. The present invention therefore provides a method for reducing the amount of said glycosylated antibody variants in an antibody preparation comprising both the Fab-glycosylated and non-glycosylated forms. The method of the invention enables both enrichment of CDR-H1 glycosylated and CDR-H1 non-glycosylated variants. If desired, the obtained antibody variants can subsequently be purified and processed for further applications.

Antigen Binding

The CDR-H1 glycosylated antibody variant described herein is capable of binding to human VEGF-A. Human vascular endothelial growth factor A (VEGF-A, UniProt Acc. No. P15692, entry version 209, Apr. 13, 2016) is a dimeric glycoprotein encoded by the VEGFA gene and is considered to be a main inducer of angiogenesis.

The terms "binding to" and "recognizing" in all grammatical forms are used interchangeably herein. The CDR-H1 glycosylated antibody variant described herein is envisaged to "specifically" bind to human VEGF-A (abbreviated "VEGF"), i.e., to bind via its antigen binding site more readily to its intended target antigen (human VEGF-A) than to a random, unrelated non-target antigen, thereby enabling selective antigen binding and reducing off-target effects.

The CDR-H1 glycosylated antibody variant described herein can also be described in terms of its binding affinity to human VEGF-A. The term "binding affinity" refers to the strength of the binding of an individual epitope with an antigen-binding domain (and in particular the CDRs of the antibody). The affinity of a given binding molecule to its specific epitope is often determined by measurement of the association rate constant (ka) and dissociation rate constant (kd) and calculating the quotient of kd to ka (equilibrium dissociation constant $K_D$=kd/ka). Means and methods for determining antibody binding affinities are readily available in the art, e.g. by using the BiaCore™ surface plasmon resonance (SPR) assay as described in the appended Examples. As compared to a non-CDR-H1 glycosylated antibody variant, CDR-H1 glycosylated antibody variants are envisioned to exhibit a reduced binding affinity to human VEGF-A.

The CDR-H1 glycosylated antibody variant described herein competes for binding to human VEGF-A with the antibody bevacizumab. Bevacizumab has been described elsewhere herein. Binding competition can be assessed by ELISA, flow cytometry or surface plasmon resonance (SPR) based assays. The term "competes for binding to human VEGF-A with bevacizumab" means that the CDR-H1 glycosylated antibody variant decreases bevacizumab binding to VEGF-A as ascertainable using the above-mentioned methods, preferably because the variant (specifically) binds to the same epitope on human VEGF-A as does bevacizumab. It is therefore envisaged to exert biological effector functions that are comparable to those of bevacizumab.

For SPR based assays, the ligand (human VEGF-A) is immobilized on an SPR sensor surface, and the binding of bevacizumab in the presence of CDR-H1 glycosylated antibody variants is assayed, e.g. as described by de Mol NJ Methods Mol Biol. 2010; 627:101-11. Flow cytometry-based assays have been described in the art, e.g. Cedeño-Arias et al., Sci Pharm. 2011 July-September; 79(3): 569-581.

As set out elsewhere herein, it is particularly envisioned that the CDR-H1 glycosylated antibody variant is a CDR-H1 glycosylated bevacizumab variant.

Biological Functions

Without wishing to be bound by specific theory, bevacizumab and antibodies competing for binding to human VEGF-A are considered "neutralizing" antibodies that reduce VEGF-A availability and, hence, block its biological effects, such as the VEGF-dependent proliferation of HUVEC cells (ascertainable by standard cell proliferation assays, see Example 4.7). It is envisaged that the CDR-H1 glycosylated antibody variants to be removed from the overall preparation using the inventive methods may show a reduced capability of inhibiting VEGF-dependent proliferation of HUVEC cells.

Constant Regions

The terms "CL", "CL region" and "CL domain" are used interchangeably herein to refer to the constant region of the light chain. The terms "CH", "CH region" and "CH domain" are used interchangeably herein to refer to the constant region of the heavy chain which comprises the "CH1", "CH2", and "CH3" regions or domains. By convention, the numbering of the constant region domains increases as they become more distal from the antigen binding site or amino-terminus of the antibody. The N-terminal portion is a variable region, and the C-terminal portion is a constant region; the CH3 and CL regions actually comprise the carboxy-terminus of the heavy and light chain, respectively.

Light Chain Constant Regions

Light chains are classified as either kappa or lambda (κ, λ). Each heavy chain class may be bound with either a kappa or a lambda light chain. In general, the light and heavy chains are covalently bonded to each other, and the "tail" portions of the two heavy chains are bonded to each other by covalent disulfide linkages or non-covalent linkages.

Heavy Chain Constant Regions+Isotypes

Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes often have ADCC activity.

The fragment crystallizable region (Fc region) is the tail region of an antibody that interacts with Fc receptors and the complement system. In IgG, IgA and IgD antibody isotypes, the Fc region is composed of the CH2 and CH3 regions of each of the two heavy chains, IgM and IgE Fc regions contain three CH regions (CH2-CH4) of each of the two heavy chains. Fc binds to various cell receptors and complement proteins. In this way, it mediates different physiological effects of antibodies (detection of opsonized particles; cell lysis; degranulation of mast cells, basophils, and eosinophils; and other processes).

Glycosylated antibody variants to be "sorted out" with the method of the invention may particularly be IgG antibodies, such as IgG1 or IgG2.

Fc-Mediated Effector Functions

The constant domains of the light chain (CL) and the heavy chain (CH1, CH2, or CH3), and in particular the Fc region, confer important biological ("Fc mediated") effector functions such as secretion, Fc receptor binding, complement-dependent cytotoxicity (CDC), antibody-dependent cell-mediated cytotoxicity (ADCC) and the like. For antibody therapeutics, avoiding effector functions such as ADCC and complement-dependent cytotoxicity (CDC) might reduce the side effects, or increasing effector functions might increase the efficacy. The choice of effector-function profile of an antibody therapeutic can be guided by consideration of the target antigen, therapeutic strategy and clinical setting.

ADCC

ADCC is a cytolytic effector mechanism of antibodies directing immune effector cells, primarily natural killer (NK) cells, to antigen-expressing cells. This mechanism relies on the engagement of FcγRs (FcγRIIIa in humans) and recruitment of immune effector cells in an Fc-dependent manner, leading to the destruction of target cells by exocytosis of the cytolytic granule complex perforin/granzyme from NK cells.

Several amino acid mutations have been attributed to improved binding to FcγRIIIa and enhanced capacity for ADCC, including Fc variants with up to three mutations selected from S298A, E333A, and K334A, numbered according to the EU index, up to five mutations selected from F243L, R292P, Y300L, V305I and mutations at the following positions: S239D, A330L, and I332E. The CDR-H1 glycosylated antibody variant may comprise one or more mutations in the Fc region that increase ADCC activity, e.g. selected from the aforementioned mutations or any other mutation that enhances ADCC as ascertainable by routine techniques known in the art, e.g. as described by Cheng et al. *J Immunol Methods.* 2014 414:69-81.

The aforementioned mutations are thought to confer an enhanced ADCC activity by strengthening the binding to FcγRs, most importantly FcγRIIIA. However, other mutations in the Fc region increasing FcγR binding are also envisaged herein. Their effect on Fc binding can be readily determined utilizing recombinant soluble FcγR and detecting antibody binding using surface plasmon resonance and/or flow-cytometry based methods, see Harrison et al. *J Pharm Biomed Anal.* 2012 Apr. 7; 63:23-8.

For some antibody therapies, antigen binding may be sufficient for achieving efficacy, and effector functions may be unnecessary or even undesirable. It is therefore also envisaged that the CDR-H1 glycosylated antibody variant may include one or more mutations in the Fc region that decrease ADCC activity. For instance, Fc mutations that have been reported to decrease FcγR binding and ADCC activity include L234A and L235A mutations, a N297A mutation leading to deglycosylation of the Fc part.

FcRn Binding

The neonatal Fc receptor (FcRn) is a MHC class I like molecule that functions to protect IgG and albumin from degradation, and improving the affinity of the FcRn-Ig interaction can thus extend the half-life antibodies, in particular of the IgG type. Various Fc mutations have been reported to improve binding of human IgG to FcRn, including Thr250Gln:Met428Leu("CL") and Met428Leu: Asn434Ser ("LS").

It is also envisioned that the CDR-H1 glycosylated antibody variant comprises one or more mutations that increase binding to FcRn. An in vitro FcRn binding assay has been described by Wu et al., *J Immunol Methods.* 2015 420:31-7.

Monoclonal Antibodies

The glycosylated antibody variants described herein may be monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. In contrast to conventional (polyclonal) antibody preparations that typically include different antibodies directed against different epitopes, monoclonal antibodies contain substantially similar epitope binding sites and are therefore typically directed against the same epitope on an antigen. Methods for producing monoclonal antibodies are known in the art. The term "monoclonal antibody" thus includes for instance recombinant, chimeric, humanized, human, or Human Engineered™ monoclonal antibodies.

Chimeric Antibody

The term "chimeric antibody," as used herein, refers to an antibody containing sequences derived from two different antibodies which typically originate from different species. Specifically, the term refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

In other words, the term "chimeric antibody" refers to any antibody wherein the antigen-binding site is obtained or derived from a first species and the constant region (which may be intact, partial or modified as described elsewhere herein) is obtained from a second species. E.g., the antigen binding site may be derived from a non-human animal (e.g., mouse or primate), whereas the constant region may be a human constant region. Typically, many chimeric antibodies comprise human and murine antibody fragments, generally human constant and mouse variable regions.

Humanized Antibody

Particularly envisaged herein are humanized CDR-H1 glycosylated antibody variants. A "humanized antibody" is generally defined as one that is (i) derived from a non-human source (e.g., a transgenic mouse which bears a heterologous immune system), which antibody is based on a human germline sequence; or (ii) CDR-grafted, wherein the CDRs of the variable region are from a non-human origin, while one or more framework regions and/or part of the CDR sequence of the variable region are of human origin and typically the constant region (if any) is of human origin.

The term "humanized antibody" thus includes antibodies in which the variable region in either the heavy or light chain or both of a human antibody is altered by at least partial replacement of one or more CDRs from a non-human antibody of known specificity and, if necessary, by partial framework region replacement and sequence changing. In other words, an antibody in which one or more "donor" CDRs from a non-human antibody (such as mouse, rat, rabbit or non-human primate antibody) of known specificity is grafted into a human heavy or light chain framework region, is referred to herein as a "humanized antibody". In some cases, it is not necessary to replace the complete CDRs with the CDRs from the donor variable domain to transfer the antigen binding capacity of one variable domain to another. Rather, transfer of some key amino acid residues may suffice to maintain the antigen binding capacity of the donor CDRs.

The framework regions within the variable region in a heavy or light chain, or both, of a humanized antibody may comprise only residues of human origin, in which case these framework regions of the humanized antibody are referred to as "fully human framework regions". A human framework region (FR) that comprises a mixture of human and donor framework residues is referred to herein as a "partially human framework region. Furthermore, humanized antibodies may comprise residues that are found neither in the recipient antibody nor in the donor antibody. These modifications are made to further refine antibody performance (e.g., to obtain desired affinity).

In general, a humanized antibody will thus comprise substantially all of at least one, and typically two, variable regions, in which all or part of the CDRs correspond to those of a non-human antibodies and all or substantially all of the FRs are those of a human antibody sequence. The humanized antibody optionally also will comprise at least a portion of an antibody constant region, typically that of a human antibody.

Human Antibody

A "human" antibody is hereby defined as one that is not chimeric or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising an amino acid sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

Bevacizumab

The CDR-H1 glycosylated antibody variant to be subjected to the method of the invention can be e.g. bevacizumab. Bevacizumab and methods for preparing the same are described in U.S. Pat. No. 6,054,297. Bevacizumab has also been described, i.a., in Ferrara et al. *Nature Reviews Drug Discovery* 3, 391-400 (May 2004).

Fragments

The term "CDR-H1 glycosylated antibody variant" also encompasses antibody fragments. The term "antibody fragment" in general refers to a polypeptide derived from a "parent" antibody and retaining its basic structure and function. An antibody fragment is hence preferably capable of binding to its target antigen, i.e. human VEGF-A. Furthermore, an antibody fragment according to the invention comprises the minimum structural requirements of an antibody which allow for antigen binding. This minimum requirement may e.g. be defined by the presence of at least the three light chain CDRs (i.e. CDR1, CDR2 and CDR3 of the $V_L$ region, i.e. CDR-L1, CDR-L2 and CDR-L3) and/or the three heavy chain CDRs (i.e. CDR1, CDR2 and CDR3 of the $V_H$ region, i.e. CDR-H1, CDR-H2 and CDR-H3). In other words, the term "antibody fragment" refers to a "functional" or "antigen-binding" polypeptide that retains the antigen-binding site (i.e. the CDRs and optionally (part of) the FR) of a "parent" antibody. Antibody fragments can be derived from, e.g., monoclonal, recombinant, chimeric, humanized and human "parent" antibodies.

In accordance with the foregoing, antibody fragments to be sorted out with the method of the present invention particularly comprise a CDR-H1 shown in SEQ ID NO: 1 (SGYTFTNYGMN), a CDR-H2 shown in SEQ ID NO: 2 (WINTYTGEPTYAADFKR), a CDR-H3 shown in SEQ ID NO: 3 (YPHYYGSSHWYFD), a CDR-L1 shown in SEQ ID NO: 4 (SASQDISNYLN), a CDR-L2 shown in SEQ ID NO: 5 (FTSSLHS) and a CDR-L3 shown in SEQ ID NO: 6 (QQYSTVPWT).

Antibody fragments envisaged herein comprise Fab, Fab', F(ab')2, scFV, di-scFv, VHH or VH. The antigen-binding fragment (Fab) comprises one antigen-binding site consisting of a set of complementarity determining regions (the complete variable domain of one heavy and one light chain). F(ab')2 fragments comprise both antigen-binding sites, as they are obtained upon cleavage below the hinge region. Fab' is analogous to the Fab fragment and it is obtained by mild reduction of F(ab')2. Single-chain variable fragments (scFv) are fusion products of antibody $V_H$ and $V_L$ regions, connected with a short linker peptide of typically ten to about 25 amino acids. Divalent (or bivalent) single-chain variable fragments (di-scFvs, bi-scFvs) comprise two scFvs joined together. Heavy-chain single domain antibodies consist only of two (VHH) or one (VH) antibody heavy chains. The term "antibody fragment" also encompasses bi- or multi/polyvalent antibody constructs generated by joining two or more of the aforementioned antibody fragments together.

Antibody Preparation

The method according to the present invention yields an antibody preparation with a reduced amount of the CDR-H1 glycosylated antibody variant. The term "antibody preparation" refers to a plurality of anti-human VEGF antibodies sharing a common amino acid sequence and structure and optionally being present in a suitable solvent or buffer, e.g. such as those described in the context of the pharmaceutical composition.

Preferably, the amount of CDR-H1 glycosylated antibodies is 10% by weight or less, such as 9% by weight or less, 8% by weight or less, 7% by weight or less, 6% by weight or less, 5% by weight or less, 4% by weight or less, 3% by weight or less, 2% by weight or less, 1% by weight or less, 0.9% by weight or less, 0.8% by weight or less, 0.7% by weight or less, 0.6% by weight or less, 0.5% by weight or less, 0.4% by weight or less, 0.3% by weight or less, 0.2% by weight or less, or 0.1% by weight or less in the obtained antibody preparation. The amount of non-CDR-H1 glycosylated antibodies in the obtained antibody formulation is thus preferably 90% by weight or higher, such as 91% by weight or higher, 92% by weight or higher, 93% by weight or higher, 94% by weight or higher, 95% by weight or higher, 96% by weight or higher, 97% by weight or higher, 98% by weight or higher, 99% by weight or higher, 99.1% by weight or higher, 99.2% by weight or higher, 99.3% by weight or higher, 99.4% by weight or higher, 99.5% by weight or higher, 99.6% by weight or higher, 99.7% by weight or higher, 99.8% by weight or higher, or 99.9% by weight or higher. Such an antibody preparation obtained by the inventive method is said to "predominantly" or "substantially" comprise non-CDR-H1 glycosylated antibody variants. The present invention encompasses an antibody preparation as disclosed herein. The present invention contemplates an antibody preparation comprising an antibody comprising a CDR-H1 having the amino acid sequence shown in SEQ ID NO:1 (SGYTFTNYGMN), wherein 10% or less by weight or any number defined hereinabove of the antibody are a CDR-H1 glycosylated antibody variant. The antibody may be any antibody disclosed herein. Particularly, the antibody may comprise the CDR sequences disclosed herein, or may comprise the VH and VL sequences as disclosed herein, or the antibody may be bevacizumab.

The method of the invention typically yields an antibody preparation comprising non- or substantially non-CDR-H1 glycosylated antibodies in "isolated" or "substantially pure" form. "Isolated" or "substantially pure" when used herein means that the antibodies have been separated and/or recovered from a component of its production environment, such that the "isolated" antibodies are free or substantially free of other contaminant components from its production environment that might interfere with its therapeutic or diagnostic use. Contaminant components may include enzymes, hormones, and other proteinaceous or non-proteinaceous solutes.

Derivatives

The antibodies in the obtained preparation can be subjected to various modifications for further applications. Such antibodies modified to alter or to introduce a functionality are designated "antibody derivatives" hereinafter. Modifications are introduced after obtaining the antibodies from the preparation predominantly comprising non-CDR-H1 glycosylated antibody variants. Various methods for post-translationally modifying antibodies are known in the art. For instance, antibodies can be subjected to treatment with organic derivatizing agents capable of reacting with selected side chains or the N- or C-terminal amino acid residues. Derivatization of binding molecules can be used to attach diagnostic or therapeutic agents (drugs), labels, or groups extending the serum half-life of the antibody, or to post-translationally alter amino acids.

Antibody-Drug Conjugates

Additional functions can be endowed on antibodies by conjugation to other drugs (such as small molecule compounds), yielding antibody-drug conjugates ("ADCs"). ADCs are tripartite antibody derivatives comprising an antigen-specific antibody conjugated to a drug via a linker. ADCs typically utilize monoclonal antibodies (mAbs) or their fragments to specifically bind target antigens and deliver a cytotoxic agent. ADCs are thought to bind to their target antigens and become internalized through receptor-mediated endocytosis, which results in subsequent release of the cytotoxin, and, eventually, apoptotic cell death of the target cell.

Linkers are preferably designed to be stable in the blood stream (to conform to the increased circulation time of antibodies) and labile at the target site to allow rapid release of the drug. Parameters taken into consideration when designing a suitable linker typically include cleavability of the linker and the position and mechanism of linkage (i.e. conjugation chemistry). Existing linkers are traditionally classified as cleavable or non-cleavable linkers.

Cleavable linkers exploit the change in environment upon internalization of the ADC-antigen complex into target cells, resulting in cleavage of the linker and release of the drug into the target cell. Exemplary cleavable linkers that are contemplated for use with the ADCs provided herein include hydrazone, disulfide and peptide linkers. In contrast to cleavable linkers that rely on distinctive intracellular conditions to release the drug, non-cleavable linkers such as thioether linkers depend solely on the process of proteolytic degradation following ADC-antigen internalization and processing in the lysosomal pathway. Linkers for antibody-drug design are well-known in the art and have been reviewed, i.a., by Peters and Brown, Biosci Rep. 2015 August; 35(4): e00225. One or several drugs can be linked to each antibody in order to achieve adequate therapeutic efficacy.

In general, any drug can be conjugated to the antibody obtained according to the inventive method, as long as it is preferably sufficiently stable to prevent its premature release before reaching the desired target cell, thereby preventing damage to non-target cells and increasing availability at the target site. As the drug is most commonly released in the lysosome following cleavage of the linker molecule, it is important to ensure that the drug remains stable in low pH environments and has the capacity to move into the cytosolic or nuclear compartments of the cell where it takes effect. Similarly, it is desirable that the molecular structure of the drug allows for its conjugation to the linker while avoiding immunogenicity, maintaining the internalization rate of the antibody and promoting or at least not compromising its biological effects, if any (i.e., ADCC, CDCC and CDC). Regardless of the stability of the drug, only a small portion of the administered ADC will typically reach the target cells. Thus, the conjugated drug is preferably potent at low concentrations.

Suitable drugs envisaged for preparing the ADCs of the invention include all cytotoxins commonly utilized in ADCs to date. Most classes of cytotoxins act to inhibit cell division and are classified based on their mechanism of action. Exemplary cytotoxins that are conceivable as part of the inventive ADCs include, without limitation, anthracycline, doxorubicin, methotrexate, auristatins including monomethyl auristatin E (MMAE) and monomethyl auristatin F (MMAF), maytansines and their maytansinoids derivatives (DMs), calicheamicins, duocarymycins and pyrrolobenzodiazepine (PBD) dimers.

Means and methods for preparing ADCs are described in the art and have been reviewed, i.a., by Peters and Brown (supra). Traditionally, drugs are chemically conjugated to antibodies using conventional techniques, whereby reactive portions of native amino acids are made to interact and bind a specific part of the linker molecule. Examples of reactive groups include the epsilon-amino end of lysine residues and the thiol side chains present in the partially reduced form of cysteine residues. Alternatives to conventional conjugation techniques include conjugation via (i) novel unpaired cysteine residues introduced at specific, controlled sites along the antibody using site-directed mutagenesis, (ii) microbial transglutaminases that recognize glutamine 'tag' sequences that can be incorporated into the antibody via plasmids, adding amine-containing drugs to the glutamine side chains, or (iii) non-natural amino acids, such as selenocysteine or acetylphenylalanine introduced into the antibody during transcription, that are available for conjugation with a suitable cytotoxin, for instance in the case of nucleophilic selenocysteine, a positively charged drug molecule.

In view of the above, the present invention thus provides antibody-drug conjugates consisting of antibodies obtained with the inventive method (i.e., non- or substantially non-CDR-H1 glycosylated anti-human VEGF-A antibodies) conjugated to a drug via a suitable linker. The antibodies compete for binding to human VEGF-A with bevacizumab as described elsewhere herein. The drug will be selected depending on the desired therapeutic application, and will particularly be a cytotoxic drug as exemplified above. Exemplary linkers have been described in the foregoing. The antibody-drug conjugate may for instance be used for treating or preventing neo-vascularization or pathological angiogenesis, and may thus be anti-cancer agents.

Chemical Modifications

Various chemical modifications can be introduced in order to alter antibody structure and/or function. Envisaged herein are, for instance, Glu or Gin cyclization at the N-terminus, glycation, acylation, acetylation, amidation, alkylation, etherification, deamidation (Asn to Asp or Gin to Glu), isomerization (Asp to isoAsp) or oxidation (Cys, His, Met, Tyr, Trp) reactions.

PEGylation and the Like

It might be desirable to increase the terminal half-life of the obtained antibodies to improve efficacy, to reduce the dose or frequency of administration, or to improve localization to the target. Alternatively, it might be advantageous to do the opposite—that is, to decrease the terminal half-life of said antibodies—to reduce whole-body exposure or to improve the target-to-non-target binding ratios.

The terminal half-life of antibodies and antibody fragments can be extended by endowing them with polyols such as polyethylene glycol (PEGylation), polypropylene glycol, polyoxyalkylenes, or copolymers of polyethylene glycol and polypropylene glycol, or of carbohydrates, such as hydroxyethyl starch (e.g., HESylation®) or polysialic acid (e.g., PolyXen® technology).

Fc Glycoengineering

IgG antibodies contain two N-linked oligosaccharides at the conserved asparagine 297 (N297) in the CH2 domain of the Fc part. Modifying the typical Fc glycosylation pattern (Fc glycoengineering) can be used to modulate FcγR binding and Fc-mediated effector functions (e.g., ADCC). For instance, Fc modifications for enhancing ADCC envisaged herein include increasing the bisecting N-acetylglucosamine in the Fc glycans or by reducing the fucose content. Deglycosylation can be used to yield antibodies lacking effector functions.

Different in vitro Fc engineering approaches are available using specific enzymes called glycosyltransferases. One strategy is to transfer an entire glycan structure to the antibody backbone. Another strategy is treatment of glycan structures from their terminal ends utilizing glycosidases such as sialidase or galactosidase. Sialyl- or galactosyltransferases can add terminal saccharide monomers. Glycosylation and deglycosylation may also be accomplished chemically, e.g. by attaching saccharide monomers to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine, or by exposing antibodies to trifluoromethanesulfonic acid.

Labeling

The obtained antibodies can further be modified by adding a label, yielding labelled antibody derivatives. The label can be coupled to the antibody via spacers/linkers of various lengths to reduce potential steric hindrance. The term "label" or "labelling group" refers to any detectable label. Exemplary labels include, but are not limited to isotopic labels, which may be radioactive or heavy isotopes, such as radioisotopes or radionuclides (e.g., $^3$H, $^{14}$C, $^{15}$N, $^{35}$S, $^{89}$Zr, $^{90}$Y, $^{99}$Tc, $^{111}$In, $^{125}$I, $^{131}$I); magnetic labels (e.g., magnetic particles); redox active moieties; optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluorophores or proteinaceous fluorophores; enzymatic groups (e.g., horseradish peroxidase, β-galactosidase, luciferase, alkaline phosphatase; biotinylated groups; or predetermined polypeptide epitopes recognized by a secondary reporter (e.g., leucine zipper pair sequences, binding sites for secondary antibodies, metal binding domains, epitope tags, etc.).

Affinity Tags

A further modification envisaged herein is the addition of a tag, such as an affinity tag aiding in purification and isolation of the antibody. Non-limiting examples of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag.

Pharmaceutical Composition

The present invention further provides a pharmaceutical composition comprising the antibody obtained using the inventive method, or the antibody-drug conjugate described herein, and optionally a pharmaceutically acceptable carrier.

In one aspect, the invention thus relates to a pharmaceutical composition comprising, as an active agent, said antibody or ADC. Accordingly, use of said antibody or ADC for the manufacture of a pharmaceutical composition (medicament) is also envisaged herein. The term "pharmaceutical composition" particularly refers to a composition suitable for administering to a human. However, compositions suitable for administration to non-human animals are also encompassed by the term.

The pharmaceutical composition is preferably pharmaceutically acceptable, i.e. capable of eliciting the desired therapeutic effect without causing any undesirable local or systemic effects in the recipient. Pharmaceutically acceptable compositions of the invention may in particular be sterile. Specifically, the term "pharmaceutically acceptable" may mean approved by a regulatory agency or other generally recognized pharmacopoeia for use in animals, and more particularly in humans.

The binding molecule described herein is preferably present in the pharmaceutical composition in a therapeutically effective amount. By "therapeutically effective amount" is meant an amount of the antibody or ADC that elicits the desired therapeutic effect. Therapeutic efficacy and toxicity can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

Carriers

As set out previously, the pharmaceutical composition may optionally comprise one or more (pharmaceutically acceptable) carriers. The terms "carrier" and "excipient" are used interchangeably herein to include fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, diluents, preservatives, emulsifiers, stabilizers and tonicity modifiers.

The pharmaceutical composition is particularly envisaged to be in the form of a liquid or lyophilized intravenous immunoglobulin (IVIG) or subcutaneous preparation. Exemplary suitable carriers for use in the pharmaceutical composition of the invention thus include saline, buffered saline, dextrose, sucrose, glucose, maltose, trehalose, D-sorbitol, glycine L-proline and water or mixtures thereof.

Additional Active Agents

The pharmaceutical compositions of the invention may comprise additional active agents depending on the therapeutic effect to be achieved and the disease to be treated. Selection of suitable additional active agents is within the skill and knowledge of the routine practitioner. The antibody or ADC provided herein, and the pharmaceutical composition comprising the same, are thought to be useful inhibitors of neo-vascularization or pathological angiogenesis, and therefore potential anti-cancer agents. Thus, combination with an additional active agent useful in the treatment of cancer may be desired. Additionally or alternatively, combination with other angiogenesis inhibitors (e.g., for treatment of cancer, but also macular degeneration in the eye, and other diseases that involve a proliferation of blood vessels) and/or with chemotherapy is envisaged.

Exemplary additional agents therefore include, inter alia, nitrogen mustards (e.g., mechlorethamine, cyclophosphamide, melphalan, chlorambucil, ifosfamide and busulfan), nitrosoureas (e.g., N-Nitroso-N-methylurea (MNU), carmustine (BCNU), lomustine (CCNU) and semustine (MeCCNU), fotemustine and streptozotocin), tetrazines (e.g., dacarbazine, mitozolomide and temozolomide), aziridines (e.g., thiotepa, mytomycin and diaziquone (AZQ)), cisplatin and derivatives (e.g., cisplatin, carboplatin and oxaliplatin), procarbazine, hexamethylmelamine, methotrexate, pemetrexed, fluorouracil, capecitabine. irinotecan, topotecan, etoposide, doxorubicin, mitoxantrone, teniposide, novobiocin, merbarone, aclarubicin, anthracyclines (e.g. doxorubicin, daunorubicin, pirarubicin, aclarubicin, and mitoxantrone), bleomycins, mitomycin C, mitoxantrone, actinomycin, vinca alkaloids (e.g., vincristine, vinblastine, vinorelbine, vindesine, and vinflunine), taxanes (e.g. paclitaxel, docetaxel), auristatins including monomethyl auristatin E (MMAE) and monomethyl auristatin F (MMAF), maytansines and their maytansinoids derivatives (DMs), calicheamicins, duocarymycins and pyrrolobenzodiazepine (PBD) dimers, itraconazole, carboxyamidotriazole, angiostatin, endostatin, tecogalan, tetrathiomolybdate, thalidomide thrombospondin TNP-470, CM101, IFN-α, IL-12, platelet factor-4, suramin, SU5416, thrombospondin, prolactin, linomide, tasquinimod, ranibizumab, sorafenib, sunitinib, pazopanib, everolimus.

Formulation

The pharmaceutical compositions of the invention can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in another form which is particularly suitable for the desired method of administration. As set out previously, the pharmaceutical composition of the invention will typically be in the form of a liquid or lyophilized IVIG or subcutaneous formulation.

Processes known per se for producing medicaments are indicated in $22^{nd}$ edition of Remington's Pharmaceutical Sciences (Ed. Maack Publishing Co, Easton, Pa., 2012) and may include, for instance conventional mixing, dissolving, granulating, dragee-making, levigating, emulsifying, encapsulating, entrapping or lyophilizing processes. After pharmaceutical compositions of the invention and optionally a suitable carrier have been prepared, they can be placed in an appropriate container and labeled for treatment of an indicated condition. Such labeling would for instance include amount, frequency and method of administration.

Administration

A variety of routes are applicable for administration of the pharmaceutical composition according to the present invention. Typically, administration will be accomplished parentally. Methods of parenteral delivery include topical, intraarterial, intramuscular, subcutaneous, intramedullary, intrathecal, intraventricular, intravenous, intraocular, intraperitoneal, intrauterine, intravaginal, sublingual or intranasal administration.

Medical Use

The antibody or the ADC of the invention is particularly envisaged for treating neo-vascularization or pathological angiogenesis.

The terms "treating" or "treatment" include therapeutic or prophylactic treatment of the diseases or conditions described herein. A "therapeutic or prophylactic treatment" comprises prophylactic treatments aimed at the complete prevention of clinical and/or pathological manifestations or therapeutic treatment aimed at amelioration or remission of clinical and/or pathological manifestations. The treated "subject" or "individual" or "animal" or "patient" can be any subject, particularly a mammalian subject, for whom therapy is desired. Mammalian subjects include humans, non-human primates, dogs, cats, guinea pigs, rabbits, rats, mice, horses, cattle, cows, and the like. The exact dosage of the antibody or ADC will be ascertainable by one skilled in the art using known techniques. Suitable dosages provide amounts of the antibody or ADC that are preferably both therapeutically safe and effective and may be adjusted for purpose of the treatment (e.g. remission maintenance vs. acute flare of disease), route, time and frequency of administration, time and frequency of administration formulation, age, body weight, general health, sex, diet, severity of the disease state, drug combination(s), reaction sensitivities, and tolerance/response to therapy. Suitable dosage ranges can be determined using data obtained from cell culture assays and animal studies and preferably include the $ED_{50}$.

The term "pathological angiogenesis" refers to the formation and growth of new blood vessels in the course of disease or trauma. The term "neo-vascularization" refers to the formation of new blood vessels, i.e., capillary ingrowth and endothelial proliferation in unusual sites. "Pathological angiogenesis" and/or "neo-vascularization" are typically found in so-called "angiogenic diseases" which include angiogenesis in tumors, neoplastic and/or malignant diseases, diabetic retinopathy, hemangiomas, arthritis, psoriasis. Tumors, neoplastic and/or malignant diseases may be sarcomas, carcinomas and lymphomas, preferably, lung cancer, breast cancer, ovarian cancer, fallopian tube cancer, colon cancer, (colo)rectal cancer, pancreatic cancer, prostate cancer, cervical cancer, kidney (renal) cancer, peritoneal cancer, squamous cell cancer, melanoma, glioma such as glioblastoma, or neuroblastoma and the like. Accordingly, the antibody or ADC or pharmaceutical composition described herein is particularly envisaged for treatment of the aforementioned diseases.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

EXAMPLES

Example 1: Identification and Enrichment of Low Abundant Protein Variants of Bevacizumab Enrichment of low abundant protein variants of bevacizumab was achieved by cation exchange chromatography (CEX), lectin affinity purification (LAP) and size exclusion chromatography (SEC). The resulting samples (fractions from CEX and SEC as well as the eluate from LAP) were analyzed with reversed phase liquid chromatography coupled to mass spectrometry (RP-LC-MS). The same glycopeptide was identified in all experiments and the glycosylation site was identified from SEC-enriched material via MS/MS. CEX and SEC enriched material was used for binding and activity studies, which showed an altered profile of the variant compared to the main bevacizumab form.

1.1 Cation Exchange Based Purification

Bevacizumab was applied to cation exchange chromatography (CEX) and fractions were collected. (FIG. 1A).

The peaks indicated in FIG. 1A were collected and re-analyzed by analytical CEX and RP-LC-MS to identify previously unknown variants.

1.1.1 Re-Chromatography of CEX Peak 1 with Unknown Identity.

The CEX re-chromatography (FIG. 1B) of the collected fractions peak 1 and main peak (MP) shows that they are homogeneous.

1.1.2 Middle-Down MS Identification of Glycosylation Site

Variants present in CEX peak 1 were first digested with Immunoglobulin G-degrading enzyme of *Streptococcus pyogenes* (IdeS) and then reduced. This procedure led to two Fc and two Fd fragments (i.e. 2× heavy chain fragments [243-452] and 2x heavy chain fragments [1-242]) as well as two light chains of bevacizumab. The mixture was then analyzed using RP-LC-MS and the resulting spectra for each peak averaged and deconvoluted.

An unknown peak at RT approx. 25.4 min was observed (FIG. 2A), even though in low abundance. The observed masses after deconvolution of the averaged spectra of the peak fit well to a glycosylated Fd-fragment (heavy chain [1-242] with complex-type glycosylation forms (Table 2, FIGS. 2B and 2C).

TABLE 2

Observed and calculated masses for glycosylated H[1-242] in the bevacizumab fraction 1 enriched by CEX fractionation

| Peak no. in FIG. 1 | Measured mass (Da) | Calculated mass (Da) | Assignment |
|---|---|---|---|
| 1 | 27349.7 | 27350.1 | Fd-glycosylated = H[1-242] + complex type glycan, core-fucosylated, monoantennary, mono-galactosylated, asialo |
| 2 | 27553.6 | 27553.4 | Fd-glycosylated = H[1-242] + complex type glycan, core-fucosylated, biantennary, mono-galactosylated, asialo |

TABLE 2-continued

Observed and calculated masses for glycosylated H[1-242] in the bevacizumab fraction 1 enriched by CEX fractionation

| Peak no. in FIG. 1 | Measured mass (Da) | Calculated mass (Da) | Assignment |
|---|---|---|---|
| 3 | 27716.4 | 27715.5 | Fd-glycosylated = H[1-242] + complex type glycan, core-fucosylated, biantennary, di-galactosylated, asialo |
| 4 | 27918.6 | 27918.7 | Fd-glycosylated = H[1-242] + complex type glycan, core-fucosylated, triantennary, di-galactosylated, asialo |
| 5 | 28006.7 | 28006.8 | Fd-glycosylated = H[1-242] + complex type glycan, core-fucosylated, biantennary, di-galactosylated, monosialylated |
| 6 | 28080.8 | 28080.8 | Fd-glycosylated = H[1-242] + complex type glycan, core-fucosylated, triantennary, tri-galactosylated, asialo |
| 7 | 28371.9 | 28372.1 | Fd-glycosylated = H[1-242] + complex type glycan, core-fucosylated, triantennary, tri-galactosylated, monosialylated |
| 8 | 28573.5 | 28575.3 | Fd-glycosylated = H[1-242] + complex type glycan, core-fucosylated, tetraantennary, tri-galactosylated, monosialylated |

1.1.3 Bottom-Up MS Identification of Glycosylation Site

To further narrow the area of glycosylation, the CEX peak 1 was digested with LysC to the peptide level. The peptides were further digested with the exoglycosidases neuraminidase (sialidase), β-galactosidase and N-acetylglucosidase to reduce complexity of the glycosylation and facilitate identifications. The exoglycosidase treatment generally reduces the complex glycan structures to an N-linked fucosylated core-glycan consisting of dHex1HexNAc2Hex3, which leads to an increase in average mass of +1039 Da compared to the unmodified (non-glycosylated) peptide.

The reduced and alkylated mixture was analyzed using RP-LC-MS and a modified (glycosylated) peptide H[1-43] containing the CDR-H1 region of the antibody was identified, together with the unmodified peptide. Calculated masses and retention times for the observed charge species are shown in Table 3.

TABLE 3

Measured and calculated masses for modified peptide H[1-43]

| RT [min] | Obs. m/z (MH[3+], monoisotopic) | Obs. peptide mass | Calc. m/z | Calc. peptide mass | Peptide (alkylated) |
|---|---|---|---|---|---|
| 62.3 | 1514.7439 | 4541.21 | 1514.7479 | 4541.22 | H[1-43], unmodified |
| 59.5 | 1860.8801 | 5579.60 | 1860.8730 | 5579.60 | H[1-43] + dHex1HexNAc2Hex3 |

H = heavy chain

1.2 Lectin Enrichment

For further investigations, affinity purification with agarose bound lectins (LAP) was used as lectins specifically bind carbohydrate moieties of different configurations and can thus be used to enrich glycosylated proteins.

Antibody samples were de-glycosylated at the common Fc-glycosylation site using PNGase-F to reduce sample complexity. It was observed that the CDR-H1 glycosylation was resistant to deglycosylation with PNGaseF. Moreover, the samples were de-sialylated using neuraminidase in order to reduce the heterogeneity of the CDR-H1 glycosylation to mostly galactosylated species. Afterwards, the CDR-H1-glycosylated fraction was purified by LAP using Erythrina Cristagalli Lectin (ECL; agarose bound lectin specific for terminal galactose) affinity chromatography. The material was then further characterized using SEC and RP-LC-MS.

1.2.1 Middle-Down MS Identification of Glycosylation Site

The LAP-enriched material was first digested using Immunoglobulin G-degrading enzyme of *Streptococcus pyogenes* (IdeS) and then reduced. This procedure resulted in two Fc fragments, two Fd fragments (i.e. 2×H[243-452] and 2×H[1-242]) and two light chains. The mixture was then analyzed using RP-LC-MS and the resulting spectra for each peak averaged and deconvoluted (FIG. 3).

The peak highlighted in the total ion chromatogram (TIC, FIG. 3A) was identified as heavy chain [1-242] with complex-type glycans linked to it. The observed masses (FIG. 3B) fit well to the calculated masses for the different glycosylation forms (Table 4). In addition also the non-glycosylated H[1-242] could be identified.

As expected, following the neuraminidase treatment needed for the LAP-enrichment no sialylated species were detected. The glycosylation pattern consists only of galactosylated mono- to tetra-antennary complex type glycans.

This analysis also proves the presence of a glycosylation site in the Fd region of the heavy chain and thus the capability of the described workflow to enrich this glycosylated species.

topic) fits to the calculated m/z value of 1631.127 for this modified peptide. The resulting observed peptide mass is 4890.37 Da, in agreement with the mass of 4890.36 Da calculated for peptide [1-43] modified with GlcNAc-Fucose (the unmodified peptide H[1-43] has a mass of 4541.22 Da, the mass shift due to the modification is +349 Da as expected).

The identified peptide contains two potential N-glycosylation sites at N31 and N35 (both in the CDR-H1 of bevacizumab). Both Asn residues are not located in any known consensus or reverse consensus glycosylation sites (Asn-X-Ser/Asn-X-Thr/Thr-X-Asn/Ser-X-Asn), where X is any amino acid).

1.3 Size Exclusion Based Purification

The bevacizumab LAP-enriched fraction was used to localize the SEC peak corresponding to the Fab-glycosylated variant in order to develop an alternative enrichment strategy based on SEC. Briefly, the LAP-enriched material was spiked into an unfractionated bevacizumab sample at different concentrations and a corresponding increase of the peak left of the main SEC peak was observed (FIG. 5).

Enrichment of glycosylated variants via preparative SEC runs was conducted to isolate the shoulder left of the main peak (AP1) as well as the main peak (MP) from a bevacizumab sample (FIG. 6A). The SEC re-chromatography of

TABLE 4

Observed and calculated masses for glycosylated H[1-242] from LAP-enriched bevacizumab

| Measured mass | Calculated mass | Identification |
| --- | --- | --- |
| 27350.5 | 27351.2 | Fd-glycosylated = H[1-242] + complex type glycan, core-fucosylated, monoantennary, mono-galactosylated, asialo |
| 27553.7 | 27553.3 | Fd-glycosylated = H[1-242] + complex type glycan, core-fucosylated, biantennary, mono-galactosylated, asialo |
| 27715.8 | 27715.5 | Fd-glycosylated = H[1-242] + complex type glycan, core-fucosylated, biantennary, di-galactosylated, asialo |
| 27918.8 | 27918.7 | Fd-glycosylated = H[1-242] + complex type glycan, core-fucosylated, triantennary, di-galactosylated, asialo |
| 28080.9 | 28080.8 | Fd-glycosylated = H[1-242] + complex type glycan, core-fucosylated, triantennary, tri-galactosylated, asialo |
| 28284.4 | 28284.0 | Fd-glycosylated = H[1-242] + complex type glycan, core-fucosylated, tetraantennary, tri-galactosylated, asialo |
| 28446.3 | 28446.2 | Fd-glycosylated = H[1-242] + complex type glycan, core-fucosylated, tetraantennary, tetra-galactosylated, asialo |
| 28811.4 | 28811.6 | Fd-glycosylated = H[1-242] + complex type glycan, core-fucosylated, tetraantennary, tetra-galactosylated, asialo, GalGlcNAc-repeat |

1.2.2 Bottom-Up MS Identification of Glycosylation Site

To determine the location of the glycosylation site, the LAP-enriched fraction was reduced, alkylated and digested with LysC to the peptide level. The peptides were further digested with the endoglycosidase F2 (Endo-F2), which cleaves between the two N-acetylglucosamine residues in the N-linked diacetylchitobiose glycan core of an oligosaccharide, generating a truncated sugar molecule with one N-acetylglucosamine residue remaining on the asparagine, hence reducing the complexity of the glycosylation. The resulting peptide mixture was analyzed using RP-LC-MS.

After Endo-F2 treatment, the complex glycan structures are reduced to an N-linked disaccharide (GlcNAc-Fucose). This leads to a modification of +349 Da to the respective unmodified peptide.

Extracted ion chromatograms for different charge variants of the modified peptides were created and a peak detected for the modified heavy chain peptide H[1-43] at RT 61.3 min (FIG. 4). The observed 3+ ion at m/z 1631.130 (monoisothe purified MP fraction is shown in FIG. 6C. The chromatogram show that the isolated material is very homogeneous and the shoulder is removed.

The SEC re-chromatography of the purified AP1 fraction is shown in FIG. 6B. The chromatogram shows that the isolated material is not homogeneous but highly enriched in AP1.

The enriched peak depicted here was used for the middle-down and bottom-up MS approaches described in chapters 1.3.2 and 1.3.3, herein below.

To obtain a pure AP1 fraction for binding and activity measurements, a SEC re-fractionation was conducted. FIG. 6C shows the re-injected fraction after the two-step fractionation workflow. This highly enriched material was then used for the target binding studies (Table 7, below) and in vitro potency study (Table 8, below).

1.3.2 Middle-Down MS Identification of Glycosylation Site

The enriched bevacizumab SEC AP1 peak was digested with IdeS, reduced and analyzed by RP-LC-MS as described previously in chapter 1.2.1. The total ion chromatogram (TIC) is shown in FIG. 7. The observed masses after deconvolution of the averaged MS spectrum corresponding to the highlighted peak in the chromatogram fit well to a glycosylated heavy chain fragment H[1-242] with complex-type glycans (Table 5, FIGS. 7C and 7D).

N ( . . . TN*Y . . . , calculated shift: 463.18 m/z). Also, the b-ion fragment of the glycosylated Asn at position 12 was detected. Calculated and observed masses are shown in Table 5. All in all 17/19 y-ions and 11/19 b-ions could be detected clearly identifying the peptide and the position of the glycosylated Asn residue.

TABLE 5

Observed and calculated masses for glycosylated H[1-242] enriched by SEC fractionation.

| Peak no. in FIG. 7 | Measured masses | Calculated masses | Identification |
|---|---|---|---|
| 1 | 27553.6 | 27553.4 | Fd-glycosylated = H[1-242] + complex type glycan, core-fucosylated, biantennary, mono-galactosylated, asialo |
| 2 | 27715.5 | 27715.5 | Fd-glycosylated = H[1-242] + complex type glycan, core-fucosylated, biantennary, di-galactosylated, asialo |
| 3 | 27918.6 | 27918.7 | Fd-glycosylated = H[1-242] + complex type glycan, core-fucosylated, triantennary, di-galactosylated, asialo |
| 4 | 28006.7 | 28006.8 | Fd-glycosylated = H[1-242] + complex type glycan, core-fucosylated, biantennary, di-galactosylated, monosialylated |
| 5 | 28080.8 | 28080.8 | Fd-glycosylated = H[1-242] + complex type glycan, core-fucosylated, triantennary, tri-galactosylated, asialo |
| 6 | 28209.9 | 28210.0 | Fd-glycosylated = H[1-242] + complex type glycan, core-fucosylated, triantennary, di-galactosylated, monosialylated |
| 7 | 28371.9 | 28372.1 | Fd-glycosylated = H[1-242] + complex type glycan, core-fucosylated, triantennary, tri-galactosylated, monosialylated |
| 8 | 28413.6 | 28413.2 | Fd-glycosylated = H[1-242] + complex type glycan, core-fucosylated, tetraantennary, di-galactosylated, monosialylated |
| 9 | 28663.3 | 28663.4 | Fd-glycosylated = H[1-242] + complex type glycan, core-fucosylated, triantennary, tri-galactosylated, disialylated |
| 10 | 28705.0 | 28704.9 | Fd-glycosylated = H[1-242] + complex type glycan, core-fucosylated, tetraantennary, di-galactosylated, disialylated |
| 11 | 28955.0 | 28954.7 | Fd-glycosylated = H[1-242] + complex type glycan, core-fucosylated, triantennary, tri-galactosylated, trisialylated |

1.3.3 Bottom-Up MS Identification of the Exact Glycosylation Site

To determine the glycosylated amino acid residue, a bottom-up approach was used in combination with Endo-F2. The enzyme cleaves after the first N-acetylglucosamine residue leaving residual GlucNAc-X (x=H or Fucose) modifications on the Asn-residues. Unlike unprocessed peptides, these peptides with residual glycosylation can be further sequenced via collision-induced dissociation (CID MS/MS) without fragmentation of the Asn-sugar bond. Using this approach the determination of glycosylated Asn-residues in consensus glycosylation sites (CGS) and non-consensus glycosylation site (NCGS) is possible (Valliere-Douglass, et al. 2009, loc.cit.).

A tryptic digests of the enriched SEC fraction AP1 was analyzed using this approach. A NCGS was in silico predicted to be located in the 19-mer peptide of bevacizumab heavy chain H[19-38]. This peptide was in fact identified in the AP1 tryptic digest with and without the residual glycosylation (FIGS. 8A, 8B and 8C) using high-resolution MS scans. In addition to the correct mass (measured: 2546.106 Da, calculated for the peptide modified with GlucNAc-Fucose: 2546.109 Da), CID MS/MS spectra were used to confirm the peptide identification and determine the exact glycosylation site.

The CID spectrum with annotation of the b- and y-fragments is shown in FIG. 8D. The y-ion series of the 19-mer clearly shows an unmodified N at position 16 of the peptide ( . . . Met Asn Trp . . . ) and a shift of 463.20 m/z at position 12 (FIG. 8D), which fits to the GlucNAc-Fuc modified

TABLE 6

Calculated/observed b- and y-ions of NCGS and unmodified H[19-38].

| AA | Obs. b-series | Calc. b-series | Calc. b-series un-modified | Obs. y-series | Calc. y-series | Calc. y-series un-modified |
|---|---|---|---|---|---|---|
| L | n.d. | 114.091 | 114.091 | 175.118 | 175.119 | 175.119 |
| S | 201.124 | 201.123 | 201.123 | 274.188 | 274.187 | 274.187 |
| C | 361.156 | 361.154 | 361.154 | 460.268 | 460.267 | 460.267 |
| A | 432.193 | 432.191 | 432.191 | 574.310 | 574.310 | 574.310 |
| A | 503.229 | 503.228 | 503.228 | 705.351 | 705.350 | 705.350 |
| S | 590.261 | 590.260 | 590.260 | 762.373 | 762.372 | 762.372 |
| G | 647.283 | 647.282 | 647.282 | 925.435 | 925.435 | 925.435 |
| Y | 810.346 | 810.345 | 810.345 | 1388.631 | 1388.615 | 1039.478 |
| T | 911.392 | 911.393 | 911.393 | 1489.664 | 1489.663 | 1140.525 |
| F | 1058.458 | 1058.461 | 1058.461 | 1636.731 | 1636.731 | 1287.594 |
| T | 1159.503 | 1159.509 | 1159.509 | 1737.777 | 1737.779 | 1388.642 |
| N* | 1622.663 | 1622.689 | 1273.552 | 1900.832 | 1900.842 | 1551.705 |
| Y | n.d. | 1785.752 | 1436.615 | 1957.859 | 1957.864 | 1608.726 |
| G | n.d. | 1842.774 | 1493.637 | 2044.886 | 2044.896 | 1695.758 |
| M | n.d. | 1973.814 | 1624.677 | 2115.931 | 2115.933 | 1766.796 |
| N | n.d. | 2087.857 | 1738.720 | 2186.937 | 2186.970 | 1837.833 |
| W | n.d. | 2273.937 | 1924.799 | 2346.959 | 2347.001 | 1997.863 |
| V | n.d. | 2373.005 | 2023.868 | n.d. | 2434.033 | 2084.895 |
| R | n.d. | 2529.106 | 2179.969 | n.d. | 2547.117 | 2197.979 |

This clearly identifies the NCGS at N31 of bevacizumab heavy chain in the CDR-H1 region.

Example 2: Target Binding and Potency Evaluation of CDR-H1 Glycosylated Bevacizumab To determine the impact of the identified glycoform on the binding of bevacizumab to VEGF, a surface plasmon resonance (SPR) based assay was performed. These studies revealed that the enriched CDR-H1 glycosylated bevacizumab obtained from CEX shows a reduced binding to VEGF with a faster dissociation kd and a higher dissociation constant $K_D$ as indicated in Table 7. Similar results were obtained for the CDR-H1 glycosylated bevacizumab SEC fraction (data not shown).

TABLE 7

VEGF binding studies by SPR

| sample | Mean ka [1/Ms] | Mean kd [1/s] | Mean $K_D$ [M] | % binding capability |
|---|---|---|---|---|
| Unfractionated reference | 2.37E+05 | 2.53E−05 | 1.07867E−10 | 100 |
| bevacizumab CEX peak 1, fraction enriched in CDR-H1 glycosylated bevacizumab | 2.26E+05 | 5.10E−05 | 2.34622E−10 | 46 |

To further investigate the impact of the glycosylation on the potency of bevacizumab, an inhibition of proliferation assay using human umbilical vein endothelial cells (HUVEC) and the highly enriched material from SEC (FIG. 6C) as described herein in the materials and methods section was performed.

TABLE 8

Determination of potency in a proliferation assay

| sample | Rel. potency (%) | 95% Rel. Fiducial limits | Result* |
|---|---|---|---|
| bevacizumab SEC AP1, highly purified CDR-H1 glycosylated bevacizumab | 17.3 | 75.4-124.4 | <50% |

*relative to reference

Bevacizumab CDR-H1 glycosylated obtained by SEC fractionation shows a significantly reduced potency (<50%) compared to the unfractionated reference material (Table 8).

Example 3: Depletion of the CDR-H1 Glycosylated Material

A bevacizumab variant with decreased potency is a potentially unwanted by-product. Thus, it is beneficial to deplete the variant by adapting the conventional antibody downstream processing scheme. Accordingly, the following exemplary options are available:
1. Alter the splitting criteria for ion exchange chromatography in the downstream process: adjust splitting criteria in a way that eliminates the undesired fraction peak 1. In the section on CEX purification it can be seen that the CDR-H1 glycosylated variant is not present in the re-injection of the main peak. Thus, by adjusting the CEX step in a conventional downstream processing, the variant can be eliminated.
2. Introduction of a SEC step in the general purification scheme. In the section on SEC purification it can be seen that the CDR-H1 glycosylated variant is not present in the re-injection of the main peak. Thus, by introducing an SEC step at the end of the downstream processing, the variant can be eliminated.

Example 4: Materials and Methods 4.1 CEX Bevacizumab Fractionation and Analysis
Semi-preparative and analytical cation-exchange chromatography (CEX) was performed by injection of bevacizumab samples onto a Dionex ProPac, semi preparative, (WCX-10, 9×250 mm) or analytical column (WCX-10, 4×250 mm). Separation was performed using a sodium phosphate buffer as eluent and a sodium chloride gradient.
4.2 Lectin Enrichment of Fab Glycosylated Bevacizumab
Bevacizumab samples were de-glycosylated at the common Fc-glycosylation site (N303) using PNGase-F. Initial experiments revealed that the PNGase-F enzyme does not seem to cleave the Fab-glycans. Mass spectrometric experiments indicated that the Fab-glycosylated variants consist mainly of galactosylated and partly sialylated glycans. Therefore, the samples were de-sialylated using neuraminidase together with PNGase-F in order to reduce the heterogeneity of Fab-glycosylated variants to mostly galactosylated species. The partially deglycosylated and desialylated antibody was cleaned from the removed glycans and enzymes by protein A enrichment (using an HiTrap™ protein A column and the AKTA system). Afterwards, the Fab-glycosylated antibody was purified using Lectin (ECL; agarose bound Erythrina Cristagalli Lectin binding terminal galactose) affinity chromatography. The purity of this material was assessed by SEC chromatography as described below (SEC bevacizumab fractionation and analysis section).
4.3 SEC Bevacizumab Fractionation and Analysis
Bevacizumab was separated by size exclusion chromatography (SEC) on a TSK gel G3000 SWXL column using potassium phosphate as eluent. The peaks from several runs were collected and concentrated using ultrafiltration devices. For binding and activity measurements, the concentrated enriched SEC-AP1 fraction was re-fractionated in order to increase the fraction purity. The concentration of the samples was determined against a bevacizumab standard calibration curve analyzed using SEC (as described above).
4.4 Enzymatic Digestions
PNGaseF and Neuroaminidase Treatment Prior to Lectin Enrichment
Reaction buffer was added to bevacizumab samples together with PNGase F (1000 units enzyme/mg antibody) and neuroaminidase (25 units enzyme/mg antibody). The mixture was incubated at 37° C. overnight and subsequently subjected to Protein A chromatography to remove enzymes and byproducts.
LysC Digestion
Bevacizumab samples were incubated in denaturing buffer with DTT and iodoacetamide. Subsequently, digestion buffer and Lys C (approx. 1:100 w:w, enzyme:protein ratio) were added and the sample was incubated for 4 h at 37° C.
Neuraminidase, β-Galactosidase and N-Acetylglucosidase Treatment Prior to LysC Digestion
Bevacizumab was diluted 1:1 with 100 mM Tris pH 8 and sialidase (1 units/100 μL), β-galactosidase (11.8 units/mg) and N-acetylglucosidase (118 units/mg) were added and incubated overnight at 37° C. The samples were then lyophilized and processed as described.
Trypsin Digestion
Bevacizumab samples were incubated in denaturing buffer, with DTT and iodoacetamide. Digestion buffer and trypsin (approx. 1:20 w:w, trypsin:protein ratio) were added and the sample was incubated overnight at 37° C.

Endo F2 Digestion

Endo-F2 reaction buffer was added to bevacizumab samples together with Endo-F2 (approx. 0.2 or 0.02 U/mg IgG), the resulting sample was incubated overnight at 37° C.

F(Ab')$_2$ and Fc' Fragments Generation

The antibody was diluted with 100 mM Tris buffer pH 8, the appropriate volume of IdeS added (approx. 0.8-2 units/µg IgG) and the mixture was incubated for 1 h at 37° C. The generated F(ab')$_2$ and Fc' fragments were reduced in denaturing conditions with 50 mM TCEP for 30 min at 30° C.

4.5 (Nano)HPLC-MS(/MS) Analysis (nano)HPLC-MS and -MS/MS analyses were carried out using QToFs (Bruker Daltonics, Bremen, Germany) coupled to a micro-flow HPLC (Agilent 1100 and 1260 series) or an Ultimate3000 nanoflow-LC (Dionex). The reverse phase column was either C-8 (for middle down) or C-18 (for bottom-up).

4.6 VEGF Binding

To study the binding of bevacizumab to VEGF, a surface plasmon resonance (SPR) assay using Biacore™ was carried out. The interaction between bevacizumab and its target, immobilized VEGF$_{165}$, is monitored in real time. Analysis of the association and dissociation of the binding partners allows the retrieval of the kinetic parameters $k_a$ (association rate constant) and $k_d$ (dissociation rate constant), which quantifies the interaction between bevacizumab or its variants and VEGF$_{165}$. Furthermore, the equilibrium dissociation constant $K_D$ is calculated using the formula $K_D=k_d/k_a$. The results are shown in Table 6.

4.7 Inhibition of Proliferation

The biological activity of bevacizumab is measured by its ability to neutralize vascular endothelial growth factor (VEGF). Upon binding of VEGF to its receptor on endothelial cells, several responses including mitogenesis are induced. Proliferation of primary human umbilical vein endothelial cells (HUVEC) is responsive to human (h) VEGF, which can be blocked by bevacizumab. Addition of graded amounts of bevacizumab to a fixed, sub-maximal dose of hVEGF causes a decrease in the proliferation of HUVEC during an incubation period. Cell proliferation is measured by detecting intracellular ATP amount using a luminescence read out.

The results explained in the above Examples and shown in the appended Figures demonstrate a CDR-H1 non-consensus glycosylation at N31 of bevacizumab's heavy chain. CEX (Example 1.1), Lectin (Example 1.2), and SEC (Example 1.3) enrichment all facilitate characterization of this novel glycosylation.

Post enrichment, it was possible to determine the composition and exact site of glycosylation. The structure comprises complex-type glycans with mono- to tetra-antennary arms that can also be sialylated. Differences in the detected glyco-forms result from different treatments prior to measurement and from different purities. However, the main glycoform is in all cases a complex tri-antennary type glycan, core-fucosylated, tri-galactosylated (cf. FIG. 7 and Table 9).

TABLE 9

| Calculated mass | Identification | CEX | LAP | SEC |
|---|---|---|---|---|
| 25946.0 | Fd = H[1-242] (reduced) | + | + | + |
| 27350.1 | Fd-glycosylated = H[1-242] + complex type glycan, core-fucosylated, monoantennary, galactosylated, asialo | + | + | |
| 27553.4 | Fd-glycosylated = H[1-242] + complex type glycan, core-fucosylated, biantennary, mono-galactosylated, asialo | + | + | |
| 27715.5 | Fd-glycosylated = H[1-242] + complex type glycan, core-fucosylated, biantennary, di-galactosylated, asialo | + | + | + |
| 27918.7 | Fd-glycosylated = H[1-242] + complex type glycan, core-fucosylated, triantennary, di-galactosylated, asialo | + | + | + |
| 28006.8 | Fd-glycosylated = H[1-242] + complex type glycan, core-fucosylated, biantennary, di-galactosylated, monosialylated | + | | + |
| 28080.8 | Fd-glycosylated = H[1-242] + complex type glycan, core-fucosylated, triantennary, tri-galactosylated, asialo | + | + | + |
| 28210.0 | Fd-glycosylated = H[1-242] + complex type glycan, core-fucosylated, triantennary, di-galactosylated, monosialylated | | | + |
| 28284.0 | Fd-glycosylated = H[1-242] + complex type glycan, core-fucosylated, tetraantennary, tri-galactosylated, asialo | | + | |
| 28372.1 | Fd-glycosylated = H[1-242] + complex type glycan, core-fucosylated, triantennary, tri-galactosylated, monosialylated | + | | + |
| 28446.2 | Fd-glycosylated = H[1-242] + complex type glycan, core-fucosylated, tetraantennary, tetra-galactosylated, asialo | | + | + |
| 28575.3 | Fd-glycosylated = H[1-242] + complex type glycan, core-fucosylated, tetraantennary, tri-galactosylated, monosialylated | + | | |
| 28663.4 | Fd-glycosylated = H[1-242] + complex type glycan, core-fucosylated, triantennary, tri-galactosylated, disialylated | | | + |

TABLE 9-continued

Results of MS measurement of the isolated CDR-H1-glycosylated variants

| Calculated mass | Identification | CEX | LAP | SEC |
|---|---|---|---|---|
| 28737.4 | Fd-glycosylated = H[1-242] + complex type glycan, core-fucosylated, tetraantennary, tetra-galactosylated, monosialylated | | | + |
| 28811.6 | Fd-glycosylated = H[1-242] + complex type glycan, core-fucosylated, tetraantennary, tetra-galactosylated, asialo, GalGlcNAc-repeat | | | |
| 29028.7 | Fd-glycosylated = H[1-242] + complex type glycan, core-fucosylated, tetraantennary, tetra-galactosylated, disialylated | | | + |

The exact position of the glycosylation was determined to be N31 in the heavy chain of bevacizumab using the bottom-up approach with MS/MS sequencing as described in Example 1.3.3.

Digestion with LysC or trypsin combined with Endo-F2 resulted in peptides with residual glycosylation. Including the residual glycosylation into the peptide search parameters, resulted in the identification of peptides with different length depending on the digestion enzyme used. However, both of the peptides found carried the residual GlcNAc-Fuc modification detected by LC-MS described in Examples 1.2.2 and 1.3.3. As the peptides contain two Asn-residues, in principle modification of both is possible. However, only a mono-glycosylated peptide was identified. Hydroxyl groups in the adjacent area of the Asn residue are necessary to facilitate the glycan transfer. Further analyses of the tryptic peptide using MS/MS spectra clearly support that only N31 was identified as modified Asn-residue during fragmentation (FIG. 8).

The characterized CDR-H1 glycosylated bevacizumab sample obtained from CEX was tested for target binding using SPR measurements (Table 7). The sample showed a strongly increased dissociation indicated by a $K_D$ increased by a factor of 2 compared to an unfractionated reference sample.

The potency of bevacizumab and its CDR-H1 glycosylated variant was assessed in an inhibition of proliferation assay. Here, a highly purified CDR-H1 glycosylated bevacizumab showed a strongly decreased potency (<50%) compared to the unfractionated reference sample.

Changes in the downstream process encompassing, for example, the adjustment of splitting criteria for the CEX-step and/or introducing an SEC purification step can facilitate the removal of this variant during manufacturing.

In summary, the results reveal the presence of a glycosylation site within the CDR-H1 region of bevacizumab that does not follow any known consensus rules. Target binding and anti-proliferation studies show altered behavior of the CDR-H1 glycosylated bevacizumab variant.

The invention claimed is:

1. A method for reducing the amount of a CDR-H1 glycosylated antibody variant having the amino acid sequence shown in SEQ ID NO:1 (SGYTFTNYGMN), wherein the first N is glycosylated that competes for binding to human VEGF-A with the antibody bevacizumab in a preparation comprising said antibody variant, the method comprising the following steps: (i) subjecting said preparation to cation exchange chromatography (CEX), size exclusion chromatography (SEC) or lectin affinity purification (LAP), (ii) analyzing fractions obtained in step (i) for the presence of said CDR-H1 glycosylated antibody variant by high performance liquid chromatography with mass spectrometry (HPLC-MS(/MS)); and (iii) removing fractions comprising said CDR-H1 glycosylated antibody variant having the amino acid sequence shown in SEQ ID NO:1 (SGYTFTNYGMN), wherein the first N is glycosylated.

2. The method of claim 1, further comprising changing a purification process for bevacizumab, by adjusting splitting criteria for a CEX-step and/or introducing an SEC purification step.

3. The method of claim 1, wherein the glycosylated antibody variant for binding to human VEGF-A is measured by ELISA, flow cytometry or surface plasmon resonance (SPR) assay.

4. The method of claim 1, wherein said N-glycosylation is a complex type glycosylation.

5. The method of claim 1, wherein said CDR-H1 glycosylated variant (i) has a reduced binding affinity to VEGF in comparison to a non-CDR-H1 glycosylated variant and/or (ii) shows a reduced inhibition on the VEGF-dependent proliferation of HUVEC cells in comparison to a non-CDR-H1 glycosylated variant.

6. The method of claim 1, wherein said antibody comprises a CDR-H1 shown in SEQ ID NO: 1, CDR-H2 shown in SEQ ID NO: 2, CDR-H3 shown in SEQ ID NO: 3, CDR-L1 shown in SEQ ID NO: 4, CDR-L2 shown in SEQ ID NO: 5 and CDR-L3 shown in SEQ ID NO: 6, and/or wherein said antibody comprises a VH region having the amino acid sequence shown in SEQ ID NO: 7 and a VL region having the amino acid sequence shown in SEQ ID NO: 8.

7. The method of claim 1, wherein (a) said antibody is humanized; and/or (b) said antibody is bevacizumab; and/or (c) said antibody is an antigen binding fragment; and/or (d) said antibody has an IgG isotype.

8. An antibody preparation comprising an antibody comprising a CDR-H1 having the amino acid sequence shown in SEQ ID NO:1 (SGYTFTNYGMN), wherein 10% or less by weight of the antibody are a CDR-H1 glycosylated antibody variant.

* * * * *